United States Patent [19]

Buren et al.

[11] Patent Number: 4,938,796
[45] Date of Patent: Jul. 3, 1990

[54] HERBICIDAL COMPOSITIONS OF ACYLATED 1,3-DICARBONYL HERBICIDES AND ANTIDOTES THEREFOR

[75] Inventors: Lawrence L. Buren, Cupertino; Joanna K. Hsu, Sunnyvale; Michael P. Ensminger, San Jose; Charles J. Duerksen, Visalia; Nicholas N. Poletika, Visalia; Benjamin P. Rodriquez, Visalia, all of Calif.

[73] Assignee: ICI Americas Inc., Wilmington, Del.

[21] Appl. No.: 208,269

[22] Filed: Jun. 22, 1988

Related U.S. Application Data

[63] Continuation-in-part of Ser. No. 70,015, Jul. 6, 1987, abandoned.

[51] Int. Cl.$^5$ .................. A01N 35/06; A01N 41/10; A01N 41/12
[52] U.S. Cl. ............................. 71/98; 71/88; 71/103; 71/105; 71/118; 71/123
[58] Field of Search ............... 71/98, 123, 88

[56] References Cited

U.S. PATENT DOCUMENTS

| | | |
|---|---|---|
| 3,131,509 | 5/1964 | Hoffman et al. |
| 3,959,304 | 5/1976 | Teach |
| 3,989,503 | 11/1976 | Pallos et al. |
| 4,021,224 | 3/1977 | Pallos et al. |
| 4,021,229 | 5/1977 | Arneklev et al. |
| 4,070,389 | 1/1978 | Martin |
| 4,104,302 | 8/1978 | Smith et al. |
| 4,137,070 | 1/1979 | Pallos et al. ................ 71/100 |
| 4,199,506 | 4/1980 | Howe et al. |
| 4,230,874 | 10/1980 | Pallos et al. |
| 4,256,481 | 3/1981 | Gardi et al. |
| 4,269,775 | 5/1981 | Szczepanski et al. |
| 4,294,764 | 10/1981 | Rinehart |
| 4,415,352 | 11/1983 | Pallos et al. |
| 4,415,353 | 11/1983 | Pallos et al. |
| 4,728,745 | 3/1988 | Carter et al. |
| 4,741,755 | 3/1988 | Knudsen et al. |
| 4,767,447 | 8/1988 | Lee et al. |
| 4,781,751 | 11/1988 | Chin |
| 4,783,213 | 11/1988 | Lee |
| 4,795,488 | 1/1989 | Lee |
| 4,797,147 | 1/1989 | Lee et al. |
| 4,808,720 | 2/1989 | Curtis |
| 4,838,932 | 6/1989 | Knudsen |

FOREIGN PATENT DOCUMENTS

| | | |
|---|---|---|
| 1192758 | 9/1985 | Canada |
| 0090262 | 5/1983 | European Pat. Off. |
| 0186118 | 7/1986 | European Pat. Off. |
| 2350547 | 4/1974 | Fed. Rep. of Germany |
| 51-113755 | 2/1976 | Japan |
| 51-13750 | 3/1976 | Japan |
| 2023582 | 3/1980 | United Kingdom |

Primary Examiner—Richard L. Raymond
Assistant Examiner—Brian Bembenick
Attorney, Agent, or Firm—Denis A. Polyn

[57] ABSTRACT

This invention embodies a two-part herbicidal system comprised of an acylated 1,3-dicarbonyl herbicide compound corresponding to the formula

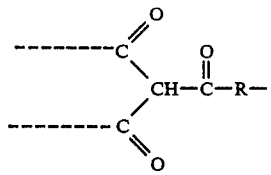

and tautomeric forms thereof wherein R is an aromatic moiety, optionally substituted, and a non-phytotoxic antidotally effective amount of an antidote therefor selected from the group of amides of haloalkanoic acids, including oxazolidines and thiazolidines, aromatic oxime derivatives, thiazole carboxylic acids and derivatives, and 1,8-naphthalic anhydride.

21 Claims, No Drawings

HERBICIDAL COMPOSITIONS OF ACYLATED 1,3-DICARBONYL HERBICIDES AND ANTIDOTES THEREFOR

CROSS REFERENCE TO RELATED APPLICATIONS

This application is a continuation-in-part of application Ser. No. 070,015, filed July 6, 1987, now abandoned.

FIELD OF THE INVENTION

This invention relates to herbicide compositions and methods of use, and more particularly, to certain herbicidal compositions comprising substituted acylated 1,3-dicarbonyl compounds and antidotes therefor which are useful as herbicides.

BACKGROUND OF THE INVENTION

An herbicide is a compound which adversely controls or modifies plant growth, e.g., killing, retarding, defoliating, desiccating, regulating, stunting, tillering, stimulating and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: preplant incorporation into the soil; in-furrow application to seeds and surrounding soil; pre-emergence surface treatment of seeded soil; post-emergence treatment of the plant and soil; and preplant seed treatment.

A manufacturer of an herbicide generally recommends a range of application rates and concentrations calculated to maximize weed control. The range of rates varies from approximately 0.01 to 50 pounds per acre (0.0111 to 56 kilograms per hectare [Kg/ha]), and is usually in the range of from 0.1 to 25 pounds per acre (0.112 to 28 Kg/ha). The term "herbicidally effective amount" describes an amount of an herbicide compound which adversely controls or modifies plant growth. The actual amount used depends upon several considerations, including particular weed susceptibility and overall cost limitations.

An important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which infest the locus of the crop.

To preserve the beneficial aspects of herbicide use and to minimize crop damage, many herbicide antidotes have been prepared. These antidotes reduce or eliminate damage to the crop without substantially impairing the damaging effect of the herbicide on weed species. See, for example, U.S. Pat. Nos. 4,021,224, 4,021,229 and 4,230,874.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continue herbicidal phytotoxicity to weed species by the herbicide, and reduced or non-phytotoxicity to the cultivated crop species. The term "antidotally effective amount" describes an amount of an antidote compound which counteracts to some degree a phytotoxic response of a beneficial crop to an herbicide.

Acylated 1,3-dicarbonyl compounds have been found to be very effective herbicides with broad general herbicidal activity against a wide range of plant species. The method of controlling vegetation with the compounds comprises applying an herbicidally effective amount of the compounds, usually with an inert carrier, to the area where herbicidal control is desired. However, the herbicidal acylated 1,3-dicarbonyl compounds have been found in some instances to adversely affect or interfere with the cultivation of a variety of crops. Therefore, the effective use of these herbicides for controlling weeds in the presence of such crops is further enhanced by, or may require in many instances, the addition of an antidotally effective amount of a compound, which is antidotally effective with the herbicide.

DESCRIPTION OF THE INVENTION

It has now been discovered that certain compounds when used in an antidotally effective amount are effective antidotes for the protection of a variety of crops from adverse herbicidal injury or the reduction of adverse herbicidal injury caused by the use of an herbicidally effective amount of an acylated 1,3-dicarbonyl carbocyclic or heterocyclic herbicidal compound.

DESCRIPTION OF THE HERBICIDE COMPOUNDS

The acylated 1,3-dicarbonyl herbicide compounds of this invention are contained within and correspond to the following general formula

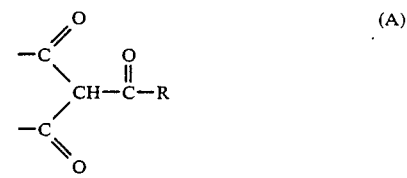

(A)

in which R is a group as hereinafter defined (and may generally be an optionally substituted aromatic moiety). Compounds of this type have been described in a number of references as being useful, for instance, as chemical intermediates and/or pesticides. The undefined remainder of the molecule represented in Formula A, which includes the dicarbonyl group, has a generally cyclical structure. In particular, the cyclical structure which is the cyclical 1,3-dicarbonyl group including a 5- to 6-member ring, which may be carbocyclic or heterocyclic which may be further optionally substituted with one or more aromatic groups.

Tautomerism is possible in the herbicide carbocyclic or heterocyclic compounds of this invention. For example, the cyclic 1,3-dicarbonyl containing herbicide compounds of this invention can have the following four structural formulae because of tautomerism:

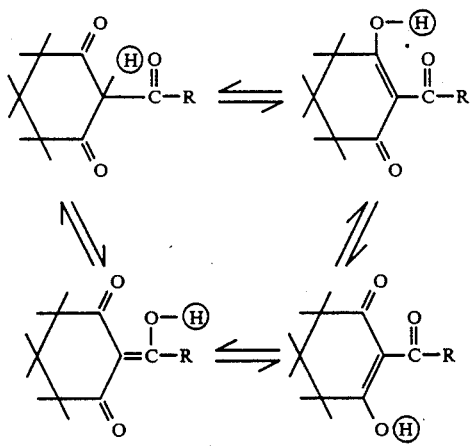

wherein the undefined substituents are as defined hereinafter. Similar tautomerism is observed for corresponding heterocyclic compounds.

The circled proton on each of the four tautomers is reasonably labile. These protons are acidic and can be removed by a base to give a salt having an anion of the following four resonant forms

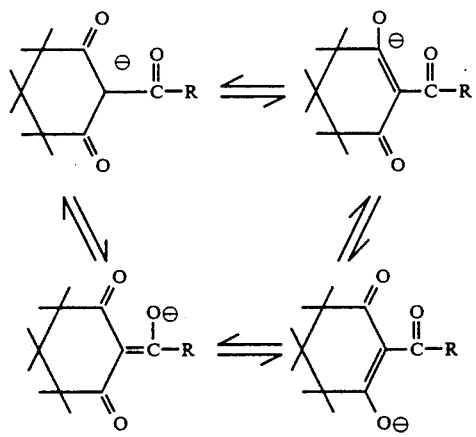

wherein the undefined further substituents are as herein below defined.

Examples of cations of these bases are inoganic cations such as alkali metals, e.g. lithium, sodium, and potassium, alkaline earth metals, e. g. barium, magnesium, calcium and strontium, or organic cations such as substituted ammonium sulfonium or phosphonium wherein the substituent is an aliphatic or aromatic group.

Acylated carbocyclic 1,3-dicarbonyl compounds of this type have the general structure

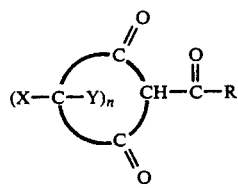
(B)

in which R is an optionally substituted aromatic moiety as hereinafter defined and n is 2 or 3, preferably 3. The ring can be unsubstituted (all X and Y groups are hydrogen), or one or more hydrogen atoms may be replaced by aliphatic, aromatic, heterocyclic or alkylene groups, particularly hydrocarbyl groups. Examples of such hydrocarbyl groups are alkyl, particularly lower alkyl, phenyl, and $C_2$-$C_5$ alkylene groups such as dimethylene, trimethylene and the like, in which case the compounds have a spiro structure. The carbocyclic ring may be saturated or unsaturated, containing an olefinic bond linking the 4- and 5-carbon atoms.

Acylated heterocyclic 1,3-dicarbonyl herbicide compounds of this invention have the general formula

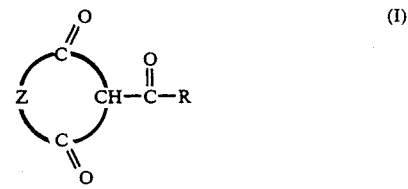
(I)

in which R is as defined herein and Z is a chain which contains 2 or 3 ring atoms, at least one of which is nitrogen, oxygen or sulfur. Nitrogen atoms in such rings may be unsubstituted or may be substituted by a $C_1$-$C_4$ alkyl group. Carbon atoms in such rings may be unsubstituted or may be substituted similarly to those in the carbocyclic compounds described above. Where possible, heterocyclic rings may be saturated or unsaturated.

Examples of heterocyclic 1,3-dicarbonyl structures include, for instance, barbituric acid derivatives, hydroxypyrones, 3,5-dioxotetrahydropyrans and -thiopyrans, cyclical oxolactones, cyclical oxothiolactones and oxalactams.

One particular class of herbicide compounds is that in which the dicarbonyl compound is an optionally susttituted cyclohexanedione and the acylating group is a substituted benzoyl moiety. That is, R in Formula B above is substituted phenyl. In general, these compounds have the formula

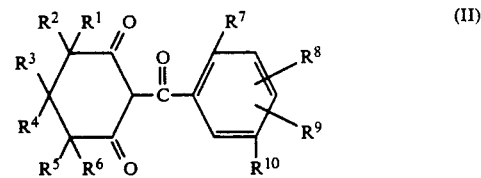
(II)

in which
$R^1$, $R^2$, $R^3$, $R^4$, $R^5$ and $R^6$ are independently hydrogen or $C_1$-$C_4$ alkyl or
$R^1$ or $R^3$ is

in which
$R_a$ is $C_1$-$C_4$ alkyl; phenyl, optionally substituted by from 2 to 5 methyl groups; or $R^3$ is hydroxyl and $R^1$, $R^2$, $R^4$, $R^5$ and $R^6$ are independently hydrogen or $C_1$-$C_4$ alkyl;
or in which $R^1$ and $R^2$, or $R^3$ and $R^4$, taken together are $C_2$-$C_5$ alkylene (such compounds have a spiro structure);
$R^7$ is halogen (chlorine, bromine, iodine or fluorine); cyano; $C_1$-$C_4$ alkyl; $C_1$-$C_4$ haloalkyl; $R_kSO_n$ in which $R_k$ is $C_1$-$C_4$ alkyl and n=0, 1 or 2; $C_1$-$C_4$ alkoxy; or nitro;

$R^8$, $R^9$ and $R^{10}$ independently are hydrogen or substituents including halogen; $C_1-C_4$ alkyl; $C_1-C_4$ alkoxy, trifluoromethoxy; cyano; nitro; $C_1-C_4$ haloalkyl; $C_1-C_4$ alkylthio; phenoxy; or substituted phenoxy in which the substituent is halogen or halomethyl or both;

$R_bS(O)n$ in which n is 0, 1 or 2; and $R_b$ is $C_1-C_4$ alkyl, $C_1-C_4$ haloalkyl, phenyl or benzyl,

in which $R_c$ is $C_1-C_4$ alkyl,

—$NR_dR_e$ in which $R_d$ and $R_e$ independently are hydrogen or $C_1-C_4$ alkyl;

$R_fC(O)$— in which $R_f$ is hydrogen, $C_1-C_4$ alkyl, $C_1-C_4$ haloalkyl or $C_1-C_4$ alkoxy;

$SO_2NR_gR_h$ in which $R_g$ and $R_h$ independently are hydrogen or $C_1-C_4$ alkyl;

or $R^8$ and $R^9$ taken together form a ring structure with two adjacent carbon atoms of the phenyl ring to which they are attached.

Compounds of this type, with various substituents on either or both of the cyclohexane or phenyl rings are disclosed in: European Patent Application, Publication No. 90262; the following copending United States patent applications, assigned to the Assignee herewith, and entitled "Certain 2-(2-Substituted Benzoyl)-1,3-Cyclohexanediones", Ser. No. 634,408, filed July 31, 1984; Ser. No. 640,791, filed Aug. 17, 1984; Ser. No. 752,702, filed July 8, 1985; and Ser. No. 722,593, filed Sept. 5, 1985; the following U.S. patent applications assigned to the Assignee hereof, Ser. No. 683,900, filed Dec. 20, 1984 and Ser. No. 802,135, filed Nov. 29, 1985, entitled "Certain 2-(2-Nitrobenzoyl)-1,3-Cyclohexanediones"; Ser. No. 683,899, filed Dec. 20, 1984, entitled "Certain 2-(2'-Cyanobenzoyl)-1,3-Cyclohexanediones"; Ser. No. 683,898, filed Dec. 20, 1984 and Ser. No. 802,133, filed Nov. 29, 1985, entitled "Certain 2-(2'-Substituted Benzoyl)-1,3-Cyclohexanediones"; Ser. No. 683,884, filed Dec. 20, 1984 and Ser. No. 802,134, filed Nov. 29, 1985, entitled "Certain 2-(2'-Alkylbenzoyl)-1,3-Cyclohexanediones" (all these patent applications relating to compounds which are herbicidal): and Japanese Patent Applications (Publication Nos.) 51/13750 and 51/13755 of Nippon Soda K. K., which disclose some compounds of this type as intermediates for herbicides. The disclosures of these documents are hereby incorporated herein.

Some specific types of such acylated heterocyclic 1,3-dicarbonyl herbicide compounds include:

barbituric acid derivatives such as those of the formula IV

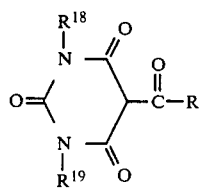

in which $R^{18}$ and $R^{19}$ are hydrogen or $C_1-C_4$ alkyl and R is substituted phenyl such as

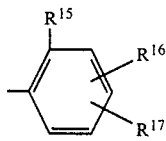

in which $R^{15}$, $R^{16}$ and $R^{17}$ are as defined hereinafter. Such compounds are described, for instance, in copending, commonly assigned United States patent application no. 872,068, filed June 9, 1986; entitled "Certain S-(2-Substituted Benzoyl)-Barbituric Acids, the disclosure of which is hereby incorporated herein;

oxolactams such as those having the formula V

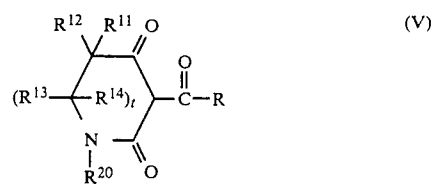

in which $R^{11}$-$R^{14}$ and $R^{20}$ are independently hydrogen or $C_1-C_4$ alkyl, or $R^{11}$ and $R^{12}$ together are $C_2-C_5$ alkylene, t is 0 or 1 and R is substituted phenyl such as

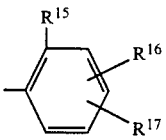

in which $R^{15}$ is hydrogen; halogen; $C_1-C_2$ alkyl; $C_1-C_2$ alkoxy; nitro; cyano; $C_1-C_2$ haloalkyl; or $R_mSO_n$ wherein $R_m$ is $C_1-C_2$ alkyl and n is 0, 1 or 2; trifluoromethyl or difluoromethyl; or trifluoromethoxy or difluoromethoxy. Preferably $R^{15}$ is chlorine, bromine, $C_1-C_2$ alkyl, $C_1-C_2$ alkoxy, trifluoromethyl, cyano, nitro, $C_1-C_2$ alkyl, $C_1-C_2$ alkoxy, trifluoromethyl, cyano, nitro, $C_1-C_2$ alkylthio or $C_1-C_2$ alkylsulfonyl; and $R^{16}$ and $R^{17}$ independently are (1) hydrogen, (2) halogen; (3) $C_1-C_4$ alkyl; (4) $C_1-C_4$ alkoxy; (5) trifluoromethoxy; (6) cyano; (7) nitro; (8) $C_1-C_4$ haloalkyl; (9) $R^bSO_n$— wherein n is the integer 0, 1 or 2; and $R^b$ is (a) $C_1-C_4$ alkyl; (b) $C_1-C_4$ alkyl substituted with halogen or cyano; (c) phenyl; or (d) benzyl. Such compounds are disclosed, for instance, in copending, commonly assigned U.S. application no. 871,973, filed June 9, 1986, entitled "Certain 3-(Benzoyl-4-Oxolactams" the disclosure of which is hereby incorporated by reference;

Herbicidal oxolactones and oxothiolactones within this invention such as those having the formula VI

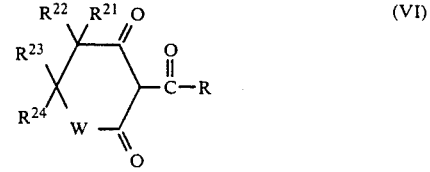

in which $R^{21}$-$R^{24}$ are independently hydrogen or $C_1-C_4$ alkyl; or $R_{21}$ and $R_{22}$ together are $C_2-C_5$ alkylene; or $R^{23}$ and $R^{24}$ together are $C_2-C_5$ alkylene; or $R^{21}$ and $R^{23}$ together form a bond, and R is substituted phenyl such as

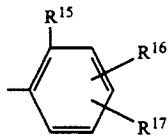

in which $R^{15}$–$R^{17}$ are as defined above; and W is oxygen or sulfur. When $R^{21}$ and $R^{23}$ together form a bond, the compounds contain an unsaturated heterocyclic ring. Such compounds are disclosed, for instance, in copending, commonly assigned U.S. application no. 871,975, filed June 9, 1986; entitled "Certain 4-Oxo-Benzoyl-Valerolactones and Thiolactones", the disclosure of which is hereby incorporated herewith;

dioxotetrahydropyrans and -thiopyrans such as those having the formula VII

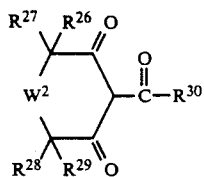

in which $R^{26}$–$R^{29}$ are independently hydrogen or $C_1$–$C_4$ alkyl or $R^{26}$ and $R^{27}$ together are $C_2$–$C_5$ alkylene, or $R^{28}$ and $R^{29}$ together are $C_2$–$C_5$ alkylene; $W^2$ is oxygen, sulfur or sulfonyl and $R^{30}$ is substituted phenyl such as

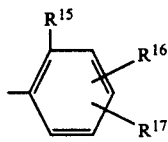

in which $R^{15}$–$C^{17}$ are as previously defined. Such compounds are described, for instance, in copending, commonly assigned U.S. application no. 872,080, filed Sept. 9, 1986, entitled "Certain Substituted 4-Benzoyl-3,5-Oxo-tetrahydropyrans and Thiopyrans".

Another embodiment of this invention is an herbicidal composition comprising a 2-(2-substituted benzoyl)-4-(substituted or unsubstituted phenyl) cyclohexanedione and an antidote with an inert carrier therefor. The 1,3-cyclohexanedione moiety is preferably substituted with groups hereinafter defined. The benzoyl and cyclohexanedione moieties can be further substituted.

Within the scope of this embodiment are compounds in which R in Formula B above is a substituted phenyl. In general, these compounds have the formula VIII:

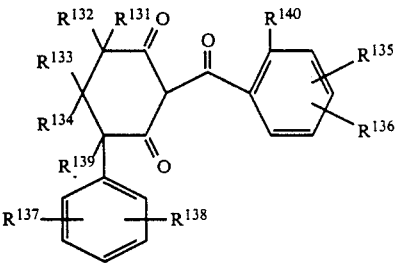

wherein $R^{140}$ is halogen; $C_1$–$C_2$ alkyl; $C_1$–$C_2$ alkoxy; trifluoromethoxy; or difluoromethoxy; nitro; cyano; $C_1$–$C_2$ haloalkyl; $R^aSO_n$— wherein n is 0 or 2; and $R^a$ is $C_1$–$C_2$ alkyl; trifluoromethyl or difluoromethyl. Of particular interest are compounds in which $R^{140}$ is chlorine, bromine, $C_1$–$C_2$ alkyl, $C_1$–$C_2$ alkoxy, trifluoromethyl, cyano, nitro, $C_1$–$C_2$ alkylthio or $C_1$–$C_2$ alkylsulfonyl; more preferably chlorine, nitro, methyl, trifluoromethyl or methylsulfonyl;

$R^{131}$ is hydrogen or $C_1$–$C_4$ alkyl;
$R^{132}$ is hydrogen or $C_1$–$C_4$ alkyl;
$R^{131}$ and $R^{132}$ together are $C_2$–$C_5$ alkylene;
$R^{133}$ is hydrogen or $C_1$–$C_4$ alkyl;
$R^{134}$ is hydrogen or $C_1$–$C_4$ alkyl;
$R^{133}$ and $R^{134}$ together are $C_2$–$C_5$ alkylene;
$R^{135}$, $R^{136}$, $R^{137}$ and $R^{138}$ independently are (1) hydrogen; (2) chlorine, fluorine or bromine; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^bSO_n$— wherein n is the integer 0, 1 or 2; and $R^b$ is
  (a) $C_1$–$C_4$ alkyl;
  (b) $C_1$–$C_4$ alkyl substituted with halogen or cyano;
  (c) phenyl; or
  (d) benzyl;
(10) —$NR^cR^d$ wherein
$R^c$ and $R^d$ independently are hydrogen or $C_1$–$C_4$ alkyl;
(11) $R^eC(O)$— wherein $R^e$ is $C_1$–$C_4$ alkyl or $C_1$–$C_4$ alkoxy;
(12) —$SO_2NR^cR^d$ wherein $R^c$ and $R^d$ are as defined; or
(13) —$N(R^c)C(O)R^d$ wherein $R^e$ and $R^d$ are as defined; and
$R^{139}$ is hydrogen or $C_1$–$C_4$ alkyl.

Preferably $R^{135}$ is in the 3-position and $R^{135}$ and $R^{137}$ are hydrogen, chlorine, fluorine, trifluoromethyl, cyano, $C_1$–$C_4$ alkoxy or $C_1$–$C_4$ thioalkyl; or $R^{135}$ and $R^{137}$ are hydrogen and $R^{136}$ and $R^{138}$ are in the 4-position; wherein $R^{136}$ and $R^{138}$ are halogen, cyano, trifluoromethyl, or $R^bSO_2$ wherein $R^b$ is $C_1$–$C_4$ alkyl or $C_1$–$C_4$ haloalkyl.

Compounds of this type are described in copending U.S. Application Ser. No. 906,462, filed Sept. 12, 1986.

Another embodiment of this invention is an herbicidal composition comprising an herbicidally active 2-(substituted benzoyl)-cyclohexanedione-1,3 and the acylating group is a substituted benzoyl moiety and an antidote with an inert carrier therefor. The 4- and 6-positions of the cyclohexanedione-1,3 moiety are preferably substituted with groups hereinafter defined, most preferably with hydrogen or methyl groups. The substituted benzoyl and cyclohexanedione-1,3 moieties can be further substituted.

Within the scope of this embodiment are the compounds in which R in Formula B, above, is substituted phenyl. In general, these compounds have the formula IX:

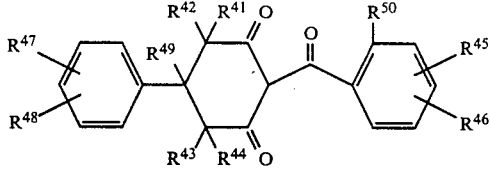

wherein
- $R^{50}$ is halogen; $C_1$–$C_2$ alkyl; $C_1$–$C_2$ alkoxy; trifluoromethoxy or difluoromethoxy; nitro; cyano; $C_1$–$C_2$ haloalkyl; $R^a SO_n$— wherein n is 0 or 2; and $R^a$ is $C_1$–$C_2$ alkyl; trifluoromethyl; or difluoromethyl;
- $R^{41}$ is hydrogen or $C_1$–$C_4$ alkyl;
- $R^{42}$ is hydrogen or $C_1$–$C_4$ alkyl;
- $R^{41}$ and $R^{42}$ together are $C_2$–$C_5$ alkylene;
- $R^{43}$ is hydrogen or $C_1$–$C_4$ alkyl;
- $R^{44}$ is hyrogen or $C_1$–$C_4$ alkyl;
- $R^{43}$ and $R^{44}$ together are $C_2$–$C_5$ alkylene;
- $R^{45}$, $R^{46}$, $R^{47}$ and $R^{48}$ independently are (1) hydrogen; (2) halogen selected from the group consisting of chlorine, fluorine or bromine; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^b SO_n$— wherein n is the integer 0, 1 or 2; and $R^b$ is
  - (a) $C_1$–$C_4$ alkyl;
  - (b) $C_1$–$C_4$ alkyl substituted with halogen or cyano;
  - (c) phenyl; or
  - (d) benzyl;
- (10) —$NR^c R^d$ wherein $R^c$ and $R^d$ independently are hydrogen or $C_1$–$C_4$ alkyl;
- (11) $R^e C(O)$— wherein $R^e$ is $C_1$–$C_4$ alkyl or $C_1$–$C_4$ alkoxy;
- (12) —$SO_2 NR^c R^d$ wherein $R^c$ and $R^d$ are as defined; or
- (13) —$N(R^c)C(O)R^d$ wherein $R^c$ and $R^d$ are as defined; and
- $R^{49}$ is hydrogen or $C_1$–$C_4$ alkyl.

Of particular interest are compounds in which $R^{45}$ is in the 3-position and $R^{45}$ is hydrogen, chlorine, fluorine, trifluoromethyl, cyano, $C_1$–$C_4$ alkoxy or $C_1$–$C_4$ thioalkyl; or $R^{45}$ is hydrogen; or $R^{46}$ is in the 4-position; and $R^{46}$ is halogen, cyano, trifluoromethyl, or $R^b SO_2$ wherein $R^b$ is $C_1$–$C_4$ alkyl, preferably methyl or $C_1$–$C_4$ haloalkyl, difluoromethyl or trifluoromethyl.

Compounds of this type are described in copending U.S. patent application Ser. No. 906,461, filed Sept. 12, 1986.

Another embodiment of this invention is an herbicidal composition comprising an herbicidally active 2-(2-substituted benzoyl)-4-(substituted oxy or substituted thio)-1,3-cyclohexanedione and an antidote with an inert carrier therefor. The 5- and 6-positions of the 1,3-cyclohexanedione moiety are preferably substituted with groups hereinafter defined, most preferably with hydrogen or methyl groups. The substituted benzoyl and cyclohexanedione moieties can be further substituted.

Within the scope of this embodiment are compounds having the following structural formula

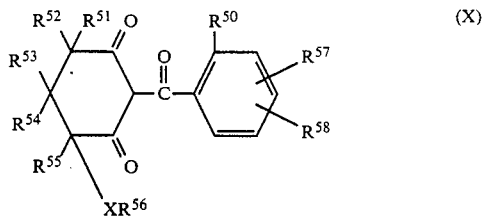

wherein
X is oxy, thio, sulfinyl or sulfonyl;
- $R^{50}$ is halogen; $C_1$–$C_2$ alkyl; $C_1$–$C_2$ alkoxy, preferably methoxy; trifluoromethoxy; difluoromethoxy; nitro; cyano; $C_1$–$C_2$ haloalkyl; $R^a SO_n$— wherein n is 0 or 2, preferably 2 and $R^a$ is $C_1$–$C_2$ alkyl; trifluoromethyl or difluoromethyl. Preferably, $R^{50}$ is chlorine, bromine, $C_1$–$C_2$ alkyl, $C_1$–$C_2$ alkoxy, trifluoromethyl, cyano, nitro, $C_1$–$C_2$ alkylthio or $C_1$–$C_2$ alkylsulfonyl; more preferably chlorine, nitro, methyl, trifluoromethyl or methylsulfonyl;
- $R^{51}$ is hydrogen; $C_1$–$C_4$ alkyl; phenyl; or substituted phenyl;
- $R^{52}$ is hydrogen or $C_1$–$C_4$ alkyl; or
- $R^{51}$ and $R^{52}$ together are $C_2$–$C_5$ alkylene;
- $R^{53}$ is hydrogen; $C_1$–$C_4$ alkyl; phenyl; or substituted phenyl with the proviso that $R^{51}$ and $R^{53}$ are not both phenyl or substituted phenyl;
- $R^{54}$ is hydrogen or $C_1$–$C_4$ alkyl;
- $R^{55}$ is hydrogen or $C_1$–$C_4$ alkyl;
- $R^{56}$ is $C_1$–$C_4$ alkyl, $C_1$–$C_4$ haloalkyl, or phenyl and
- $R^{57}$ and $R^{58}$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^b SO_n$— wherein n is the integer 0, 1 or 2; and $R^b$ is
  - (a) $C_1$–$C_4$ alkyl;
  - (b) $C_1$–$C_4$ alkyl substituted with halogen or cyano;
  - (c) phenyl; or
  - (d) benzyl;
- (10) —$NR^c R^d$ wherein $R^c$ and $R^d$ independently are hydrogen or $C_1$–$C_4$ alkyl;
- (11) $R^e C(O)$— wherein $R^e$ is $C_1$–$C_4$ alkyl or $C_1$–$C_4$ alkoxy;
- (12) —$SO_2 NR^c R^d$ wherein $R^c$ and $R^d$ are as defined; or
- (13) —$N(R^c)C(O)R^d$ wherein $R^c$ and $R^d$ are as defined.

Compounds of this type are described in copending U.S. patent application Ser. No. 919,280, filed Oct. 16, 1986.

Another embodiment of this invention is an herbicidal composition comprising an herbicidally active 2-(2-substituted benzoyl)-4-(substituted imino, oximino or carbonyl)-1,3-cyclohexanedione and an antidote with an inert carrier therefor. The 5- and 6-positions of the 1,3-cyclohexanedione moiety are substituted with groups hereinafter defined, preferably with hydrogen or methyl groups. The benzoyl and imino, oximino or carbonyl moieties can be substituted.

Also embodied within the scope of this invention are novel compounds having the following structural formula $$\text{(XI)}$$

wherein

X is oxygen or $NR^{69}$ wherein $R^{69}$ is hydrogen, $C_1-C_4$ alkyl, or $C_1-C_4$ alkoxy;

$R^{60}$ is halogen; $C_1-C_2$ alkyl; $C_1-C_2$ alkoxy; trifluoromethyl or difluoromethoxy; nitro; cyano; $C_1-C_2$ haloalkyl; $R^aSO_n$— wherein n is 0 or 2; and $R^a$ is $C_1-C_2$ alkyl; trifluoromethyl; or difluoromethyl. Preferably, $R^{60}$ is chlorine, bromine, $C_1-C_2$ alkyl, $C_1-C_2$ alkoxy, trifluoromethyl, cyano, nitro, $C_1-C_2$ alkylthio or $C_1-C_2$ alkylsulfonyl; more preferably chlorine, nitro, methyl, trifluoromethyl or methylsulfonyl;

$R^{61}$ is hyrogen; $C_1-C_4$ alkyl; phenyl; or substituted phenyl;

$R^{62}$ is hydrogen or $C_1-C_4$ alkyl; or $R^{61}$ and $R^{62}$ together are $C_2-C_5$ alkylene;

$R^{63}$ is hydrogen; $C_1-C_4$ alkyl; phenyl; or substituted phenyl, with the proviso that $R^{61}$ and $R^{63}$ are not both phenyl or substituted phenyl;

$R^{64}$ is hydrogen or $C_1-C_4$ alkyl;

$R^{65}$ is hydrogen or $C_1-C_4$ alkyl;

$R^{66}$ is $C_1-C_4$ alkyl or $C_1-C_4$ haloalkyl;

$R^{67}$ and $R^{68}$ independently are (1) hydrogen; (2) halogen; (3) $C_1-C_4$ alkyl; (4) $C_1-C_4$ alkoxy; (5) trifluoromethoxy; (6) cyano; (7) nitro; (8) $C_1-C_4$ haloalkyl, preferably trifluoromethyl; (9) $R^bSO_n$— wherein n is the integer 0, 1 or 2, preferably 2; and $R^b$ is
 (a) $C_1-C_4$ alkyl;
 (b) $C_1-C_4$ alkyl substituted with halogen or cyano;
 (c) phenyl; or
 (d) benzyl;
(10) —$NR^cR^d$ wherein
 $R^c$ and $R^d$ independently are hydrogen or $C_1-C_4$ alkyl;
(11) $R^eC(O)$— wherein $R^e$ is $C_1-C_4$ alkyl or $C_1-C_4$ alkoxy;
(12) —$SO_2NR^cR^d$ wherein $R^c$ and $R^d$ are as defined; or
(13) —$N(R^c)C(O)R^d$ wherein $R^c$ and $R^d$ are as defined.

Within this embodiment, preferably $R^{67}$ is in the 3-position and $R^{67}$ is hydrogen, chlorine, fluorine, trifluoromethyl, cyano, $C_1-C_4$ alkoxy or $C_1-C_4$ thioalkyl; and preferably $R^{68}$ is in the 4-position and $R^{68}$ is halogen, cyano, trifluoromethyl, or $R^bSO_2$ wherein $R^b$ is $C_1-C_4$ alkyl, or $C_1-C_4$ haloalkyl, preferably chloromethyl, difluoromethyl or trifluoromethyl.

Compounds of this type are described in copending U.S. patent application Ser. No. 919,278, filed Oct. 16, 1986.

Another embodiment of this invention is an herbicidal composition comprising an herbicidally active 2-(2-substituted benzoyl)-4-(substituted)-1,3-cyclohexanedione and an antidote with an inert carrier therefor. The 5- and 6-positions and the 4-position of the 1,3-cyclohexanedione moiety are preferably substituted with groups hereinafter defined, most preferably with halogen or methyl groups. The benzoyl moiety can be substituted, with the groups as hereinafter recited.

Within the scope of this embodiment are compounds having the following structural formula $$\text{(XII)}$$

wherein $R^{70}$ is halogen; $C_1-C_2$ alkyl; $C_1-C_2$ alkoxy; trifluoromethoxy; difluoromethoxy; nitro; cyano; $C_1-C_2$ haloalkyl; $R^aSO_n$— wherein n is 0 or 2; and $R^a$ is $C_1-C_2$ alkyl; trifluoromethyl or difluoromethyl. Preferably, $R^{70}$ is chlorine, bromine, $C_1-C_2$ alkyl, $C_1-C_2$ alkoxy, trifluoromethyl, cyano, nitro, $C_1-C_2$ alkylthio or $C_1-C_2$ alkylsulfonyl; more preferably chlorine, nitro, methyl, trifluoromethyl or methylsulfonyl;

$R^{71}$ is hydrogen; $C_1-C_4$ alkyl; halogen; phenyl; or substituted phenyl;

$R^{72}$ is hydrogen or $C_1-C_4$ alkyl; or $R^{71}$ and $R^{72}$ together are $C_2-C_5$ alkylene;

$R^{73}$ is hydrogen; $C_1-C_4$ alkyl; phenyl; or substituted phenyl, with the proviso that $R^{71}$ and $R^{73}$ are not both phenyl or substituted phenyl;

$R^{74}$ is hydrogen or $C_1-C_4$ alkyl;

$R^{75}$ is hydrogen, halogen or $C_1-C_4$ alkyl;

$R^{76}$ is halogen, nitro, cyano, trifluoromethyl; —C(O)$NR_2^b$ wherein $R^b$ is hydrogen or $C_1-C_2$ alkyl; and $R^{77}$ and $R^{78}$ independently are (1) hydrogen; (2) halogen; (3) $C_1-C_4$ alkyl; (4) $C_1-C_4$ alkoxy; (5) trifluoromethoxy; (6) cyano; (7) nitro; (8) $C_1-C_4$ haloalkyl; (9) $R^bSO_n$— wherein n is the integer 0, 1 or 2; and $R^b$ is
 (a) $C_1-C_4$ alkyl;
 (b) $C_1-C_4$ alkyl substituted with halogen or cyano;
 (c) phenyl; or
 (d) benzyl;
(10) —$NR^cR^d$ wherein
 $R^c$ and $R^d$ independently are hydrogen or $C_1-C_4$ alkyl;
(11) $R^eC(O)$— wherein $R^e$ is $C_1-C_4$ alkyl or $C_1-C_4$ alkoxy;
(12) —$SO_2NR^cR^d$ wherein $R^c$ and $R^d$ are as defined; or
(13) —$N(R^c)C(O)R^d$ wherein $R^c$ and $R^d$ are as defined.

Within this embodiment, preferably $R^{77}$ is in the 3-position and $R^{77}$ is hydrogen, chlorine, fluorine, trifluoromethyl, cyano, $C_1-C_4$ alkoxy or $C_1-C_4$ thioalkyl; preferably $R^{78}$ is in the 4-position and $R^{78}$ is halogen, cyano, trifluoromethyl, or $R^bSO_2$ wherein $R^b$ is $C_1-C_4$ alkyl, or $C_1-C_4$ haloalkyl, preferably chloromethyl, difluoromethyl or trifluoromethyl.

Compounds of this type are described in copending U.S. patent application Ser. No. 919,277, filed Oct. 16, 1986.

The term "$C_1$–$C_4$ alkyl" includes methyl, ethyl, n-propyl, isopropyl, n-butyl, sec-butyl, isobutyl and t-butyl. The term "halogen" includes chlorine, bromine, iodine and fluorine. The terms "$C_1$–$C_4$ alkoxy" includes methoxy, ethoxy, n-propoxy, isopropoxy, n-butoxy, sec-butoxy, isobutoxy and t-butoxy. The term "$C_1$–$C_4$ haloalkyl" includes the alkyl groups defined above under $C_1$–$C_4$ alkyl in which one or more hydrogens is replaced by chlorine, bromine, iodine or fluorine.

Salts of the above-described compounds are included within the scope of the instant invention.

One method for production of acylated dicarbonyl compounds is disclosed in European Patent Application, Publication No. 90262 and involves the reaction of an optionally substituted 1,3-cyclohexanedione with a substituted benzoyl cyanide. The reaction is carried out in the presence of zinc chloride and triethylamine.

The following is a list of sample compounds as found in the above description of active herbicides.

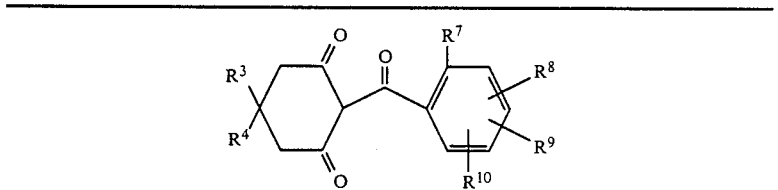

| Cmpd. No. | R3 | R4 | R7 | R8 | R9 | R10 |
|---|---|---|---|---|---|---|
| 51A | H | H | Cl | H | 4-$CH_3SO_2$— | H |
| 55A | $CH_3$ | $CH_3$ | Cl | H | 4-$CH_3SO_2$— | H |
| 90A | H | H | Cl | 3-$C_2H_5O$ | 4-$C_2H_5SO_2$ | H |

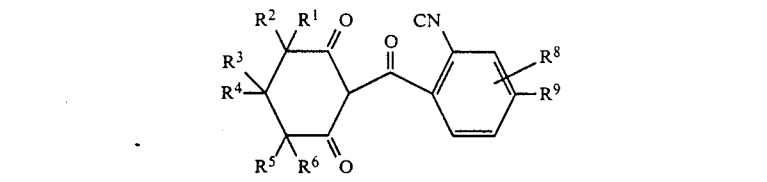

| Comp. No. | $R^1$ | $R^2$ | $R^3$ | $R^4$ | $R^5$ | $R^6$ | $R^8$ | $R^9$ |
|---|---|---|---|---|---|---|---|---|
| 1C | $CH_3$ | $CH_3$ | H | H | H | H | H | H |

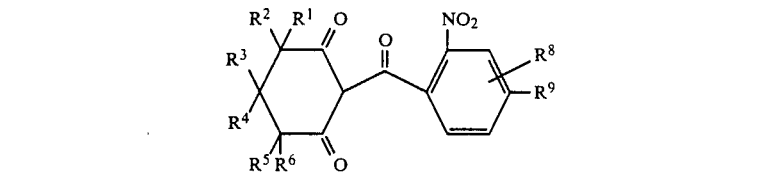

| Comp. No. | $R^1$ | $R^2$ | $R^3$ | $R^4$ | $R^5$ | $R^6$ | $R^8$ | $R^9$ |
|---|---|---|---|---|---|---|---|---|
| 4D | $CH_3$ | $CH_3$ | H | H | H | H | H | H |
| 8D | H | H | H | H | H | H | H | $CF_3$ |
| 24D | $CH_3$ | $CH_3$ | H | H | H | H | H | $SO_2CH_3$ |
| 70D | H | H | H | H | $CH_3$ | $CH_3$ | H | $SO_2CH_2Cl$ |
| 71D | $CH_3$ | $CH_3$ | OH | H | $CH_3$ | $CH_3$ | H | $CF_3$ |

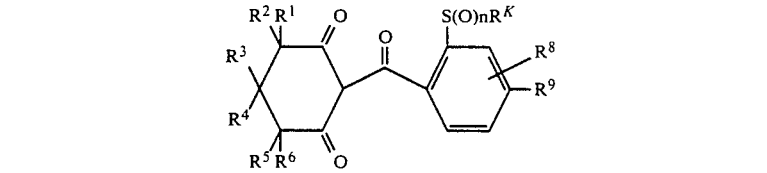

| Comp. No. | n | $R^K$ | $R^1$ | $R^2$ | $R^3$ | $R^4$ | $R^5$ | $R^6$ | $R^8$ | $R^9$ |
|---|---|---|---|---|---|---|---|---|---|---|
| 4E | 2 | $CH_3$ | $CH_3$ | $CH_3$ | H | H | $CH_3$ | H | H | H |
| 16E | 0 | $CH_3$ | H | H | H | H | H | H | H | —$SO_2$n-$C_3H_7$ |

-continued

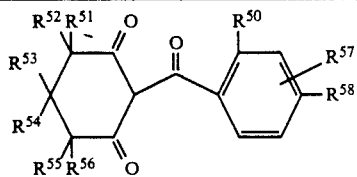

| Comp. No. | $R^{50}$ | $R^{51}$ | $R^{52}$ | $R^{53}$ | $R^{54}$ | $R^{55}$ | $R^{56}$ | $R^{57}$ | $R^{58}$ |
|---|---|---|---|---|---|---|---|---|---|
| 8F | $CH_3$ | $CH_3$ | $CH_3$ | H | H | $CH_3$ | H | H | $CH_3SO_2-$ |
| 29F | $CF_3$ | H | H | H | H | H | H | H | $C_2H_5S-$ |
| 36F | $CH_3$ | H | H | H | H | H | H | 3-Cl | $C_2H_5SO_2$ |
| 50F | $CF_3$ | $CH_3$ | $CH_3$ | H | H | H | H | H | $CF_3$ |

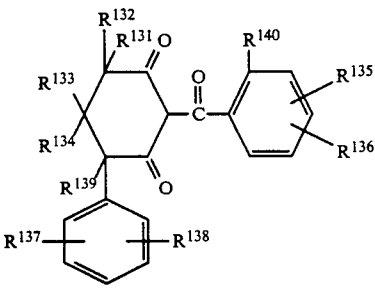

| Cmpd. No. | $R^{140}$ | $R^{131}$ | $R^{132}$ | $R^{133}$ | $R^{134}$ | $R^{135}$ | $R^{136}$ | $R^{137}$ | $R^{138}$ | $R^{139}$ |
|---|---|---|---|---|---|---|---|---|---|---|
| VIII-14 | Cl | H | H | Me | H | H | 4-$SO_2$Me | 2-F | H | H |
| VIII-17 | $NO_2$ | H | H | H | H | H | 4-Cl | 2-F | H | Me |
| VIII-24 | Cl | H | H | H | H | H | 4-$SO_2$Me | H | H | H |

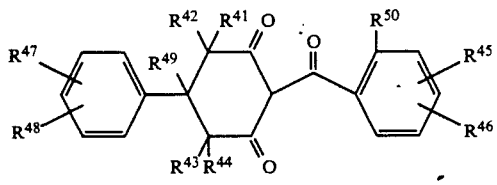

| Comp. No. | $R^{50}$ | $R^{41}$ | $R^{42}$ | $R^{43}$ | $R^{44}$ | $R^{45}$ | $R^{46}$ | $R^{47}$ | $R^{48}$ | $R^{49}$ |
|---|---|---|---|---|---|---|---|---|---|---|
| II-4 | Cl | $CH_3$ | $CH_3$ | H | H | H | 4-$SO_2CH_3$ | H | H | H |
| II-6 | $NO_2$ | H | H | H | H | H | 4-Cl | H | H | H |

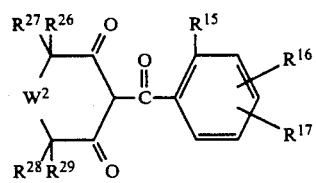

| Cmpd. No. | $R^{15}$ | $R^{26}$ | $R^{27}$ | $R^{28}$ | $R^{29}$ | $R^{16}$ | $R^{17}$ | $W^2$ |
|---|---|---|---|---|---|---|---|---|
| VII-1 | $NO_2$ | $CH_3$ | $CH_3$ | H | H | H | 4-Cl | O |
| VII-5 | Cl | H | H | H | H | H | 4-Cl | S |
| VII-7 | Cl | $CH_3$ | H | $CH_3$ | H | H | 4-Cl | S |

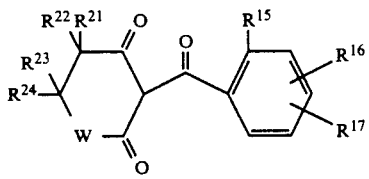

| Comp. No. | $R^{15}$ | $R^{21}$ | $R^{22}$ | $R^{23}$ | $R^{24}$ | $R^{16}$ | $R^{17}$ | W |
|---|---|---|---|---|---|---|---|---|
| VI-1 | Cl | H | $CH_3$ | bond | | H | 4-Cl | O |
| VI-4 | $NO_2$ | H | $CH_3$ | H | H | H | H | O |
| VI-9 | $NO_2$ | H | $CH_3$ | H | $CH_3$ | H | 4-Cl | O |
| VI-21 | Cl | H | $CH_3$ | H | $CH_3$ | H | 4-$SO_2CH_3$ | S |

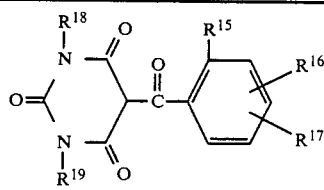

| Cmpd. No. | $R^{15}$ | $R^{18}$ | $R^{19}$ | $R^{16}$ | $R^{17}$ |
|---|---|---|---|---|---|
| IV-1 | Cl | $CH_3$ | $CH_3$ | H | 4-Cl |
| IV-6 | $NO_2$ | $CH_3$ | $CH_3$ | H | H |
| IV-13 | Cl | $CH_3$ | $CH_3$ | 3-n-$C_3H_7$ | 4-$SO_2C_2H_5$ |

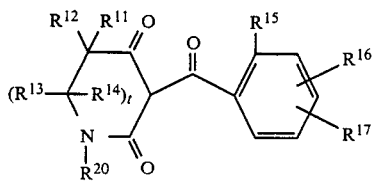

| Comp. No. | $R^{15}$ | $R^{11}$ | $R^{12}$ | $R^{13}$ | $R^{14}$ | $R^{16}$ | $R^{17}$ | $R^{20}$ | t |
|---|---|---|---|---|---|---|---|---|---|
| V-1 | $NO_2$ | H | H | H | H | H | 4-Cl | n-$C_3H_7$ | 1 |
| V-2 | $NO_2$ | H | H | n/a | n/a | H | 4-Cl | n-$C_3H_7$ | 0 |
| V-3 | Cl | H | H | H | H | H | 4-$SO_2CH_3$ | n-$C_3H_7$ | 1 |
| V-7 | $NO_2$ | H | H | $CH_3$ | $CH_3$ | H | 4-Cl | $CH_3$ | 1 |
| V-15 | $NO_2$ | $CH_3$ | H | H | H | H | 4-$SO_2CH_3$ | $C_2H_5$ | 1 |

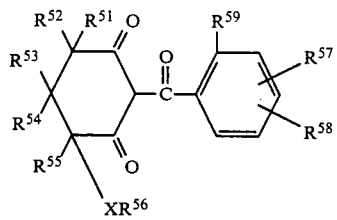

| Comp. No. | $R^{59}$ | $R^{51}$ | $R^{52}$ | $R^{53}$ | $R^{54}$ | $R^{55}$ | X | $R^{56}$ | $R^{57}$ | $R^{58}$ |
|---|---|---|---|---|---|---|---|---|---|---|
| X-5 | Cl | H | H | H | H | H | S | $CH_3$ | H | 4-$SO_2CH_3$ |
| X-6 | $NO_2$ | H | H | H | H | H | $SO_2$ | $CH_3$ | H | 4-Cl |
| X-13 | $NO_2$ | H | H | H | H | $CH_3$ | S | $CH_3$ | H | H |

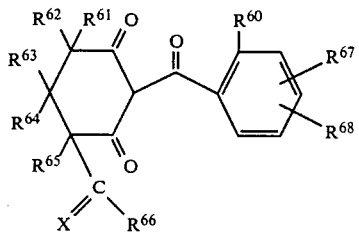

| Cmpd. No. | $R^{60}$ | $R^{61}$ | $R^{62}$ | $R^{63}$ | $R^{64}$ | $R^{65}$ | $R^{66}$ | $R^{67}$ | $R^{68}$ | X |
|---|---|---|---|---|---|---|---|---|---|---|
| XI-1 | Cl | H | H | H | H | H | $CH_3$ | H | 4-$SO_2CH_3$ | $C_2H_5$—ON |
| XI-6 | Cl | H | H | H | H | H | $CH_3$ | 3-Cl | 4-$SO_2C_2H_5$ | $CH_3$—ON |
| XI-7 | $NO_2$ | H | H | H | H | H | $CH_3$ | H | 4-Cl | $CH_3$—ON |
| XI-8 | Cl | H | H | H | H | H | $CF_3$ | H | 4-Cl | $CH_3$—ON |

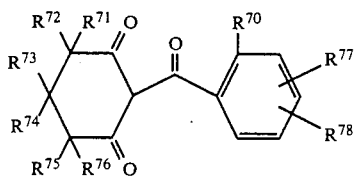

| Cmpd. No. | $R^{70}$ | $R^{71}$ | $R^{72}$ | $R^{73}$ | $R^{74}$ | $R^{75}$ | $R^{76}$ | $R^{77}$ | $R^{78}$ |
|---|---|---|---|---|---|---|---|---|---|
| XII-1 | Cl | H | H | H | H | H | Br | H | 4-$SO_2CH_3$ |
| XII-6 | $NO_2$ | $CH_3$ | $CH_3$ | H | H | H | Br | H | H |

| | | | | | | | | | |
|---|---|---|---|---|---|---|---|---|---|
| XII-7 | Cl | H | H | H | H | H | Cl | H | 4-Cl |
| XII-9 | $NO_2$ | H | H | $CH_3$ | CH | H | F | H | 4-$CF_3$ |

DESCRIPTION OF ANTIDOTES

This invention embodies a two-part herbicidal system comprised of (a) the herbicide as described hereinabove and (b) an effective antidote therefor. It has been found that such antidote compounds can be selected from a wide range of chemical substances that have been found to be effective as herbicide antidotes for the above-described acylated 1,3-dicarbonyl herbicides. The preferred compositions of this invention may include any one or more of such antidotes with the herbicides. The variety of crops on which the above-described heribicides is useful can be significantly broadened by the use of an antidote to protect one or more crops from injury therefrom and render the composition more selective against weeds. Some of the more important types of antidotes are amides of haloalkanoic acids, aromatic oxime derivatives, thiazole carboxylic acids and derivatives, and 1,8-naphthalic anhydride.

Amides of haloalkanoic acids have the generalized formula

in which R is mono- or poly-haloalkyl group. The halogens may be variously chloro, bromo or iodo; chloro and bromo are the preferred halogens, and the preferred group for R in these compounds in dichloromethyl, $Cl_2CH$—, i.e., the compounds are amides of dichloroacetic acid and amides of dibromopropionic acid. In such compounds the nitrogen is further substituted by at least one other functional group. This class of compounds also includes those in which the nitrogen forms a portion of a heterocyclic ring with substituents, as will be described below.

Antidotes of this type are described in a number of publications such as U.S. Pat. Nos. 4,021,224; 4,256,481; and 4,294,764, and British Patent 1,521,540. U.S. Pat. No. 4,021,224 contains a broad disclosure of such types of compounds and indicates a great many possibilities for mono- or di-substitution on the nitrogen atom.

Such useful antidotes include amides of haloalkanoic acids having the formula

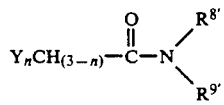

in which n is 1 or 2, Y is chlorine or bromine and $R^{8'}$ and $R^{9'}$ are independently $C_1$-$C_{12}$ alkyl, $C_2$-$C_{12}$ alkenyl, $C_1$-$C_4$ alkylene substituted with phenyl; dialkoxyalkyl wherein the alkoxy and alkyl groups each have 1–4 carbon atoms and $R^{8'}$ and $R^{9'}$ taken together are $C_1$-$C_4$ alkyleneoxyalkylene, or alkylenethioalkylene substituted with a spiro 5- to 6-membered heterocyclic ring, phenyl, alkyl, alkoxyalkyl, or alkylthioalkyl.

Preferable embodiments of said antidotes include those wherein n is 1 or 2, $R^{8'}$ and $R^{9'}$ are independently $C_1$-$C_6$ alkyl, $C_2$-$C_6$ alkenyl, dialkoxyethyl, cyclic acetal or $C_1$-$C_2$ alkylene substituted with phenyl. Further embodiments include those antidotes wherein n is 2, and $R^{8'}$ and $R^{9'}$ are independently $C_1$-$C_4$ alkyl, $C_2$-$C_4$ alkenyl, dimethyoxyethyl, dioxolanylmethyl or benzyl.

One type of antidote disclosed in U.S. Pat. No. 4,021,224 is N,N-diallyl dichloroacetamide,

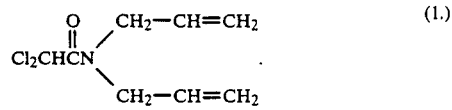

It is generally known commercially as R-25788 and is included as an antidote in several commercial products containing thiolcarbamate herbicides.

Another class of amides of haloalkanoic acids is that in which the nitrogen atom is contained in an oxazolidine or thiazolidine ring. Preferably R is dichloromethyl, and these oxazolidines and thiazolidines have the general formula

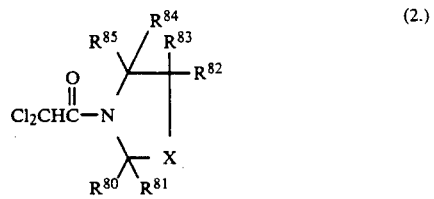

wherein $R^{80}$, $R^{81}$, $R^{82}$, $R^{83}$, $R^{84}$ and $R^{85}$ are independently hydrogen, lower alkyl, alkoxyalkyl, alkylthioalkyl, lower alkylsulfonylmethyl or -phenyl, or $R^{80}$ and $R^{81}$ taken together form an alkylene group, preferably a butylene, pentylene or hexylene group optionally substituted by one or two methyl groups and X is oxygen or sulfur. Compounds of these types are disclosed in a number of patents, including U.S. Pat. Nos. 4,021,224 and 4,256,481. Representative compounds of this type include (where not specifically mentioned the radical is hydrogen):

2-2-dimethyl-N-dichloroacetyl oxazolidine ($R^{80}$ and $R^{81}$ = methyl) (known as 7);

2,2,5-trimethyl-N-dichloroacetyl oxazolidine ($R^{80}$, $R^{81}$ and $R^{82}$ = methyl) (known as 2);

2,2-dimethyl-5-n-propyl-N-dichloroacetyl oxazolidine ($R^{80}$, $R^{81}$ = methyl, $R^{82}$ = n-propyl);

2,2-dimethyl-5-phenyl-N-dichloroacetyl oxazolidine ($R^{80}$, $R^{81}$ = methyl, $R^{82}$ = phenyl) (known as 3);

2,2-spirocyclohexyl-N-dichloroacetyl oxazolidine ($R^{80}$ plus $R^{81}$ taken together = pentamethylene); and 2,2-dimethyl-N-dichloroacetyl-5-ethyl oxazolidine ($R^{80}$, $R^{81}$ = methyl, $R^{82}$ = ethyl).

Other compounds in which $R^{80}$ and $R^{81}$ taken together are alkylene are disclosed for instance in British Patents 1,512,540 and 2,023,582 and Hungarian Patent 181,621.

A third type of haloalkanoic acid amide is disclosed generally in U.S. Pat. No. 4,294,764 and has the general formula

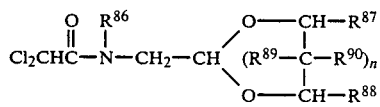
(3.)

in which $R^{86}$ may be one of a number of alkyl, alkenyl or alkynyl moieties; $R^{87}$, $R^{88}$, $R^{89}$ and $R^{90}$ are independently hydrogen or methyl; and n is 0 or 1. A representative compound of this type is the compound N-(1,3-dioxolan-2-yl-methyl)-N-(2-propenyl)-2,2-dichloroacetamide, which has the formula

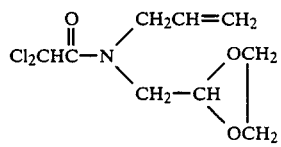
(4.)

This corresponds to the previous formula (3) in which $R^{86}$ is 2-propenyl, $R^{87}$ and $R^{88}$ are both hydrogen and n is 0.

Oxime derivatives which are suitable for use as antidotes with herbicides are disclosed, for instance in U.S. Pat. Nos. 4,070,389 and 4,269,775 and have the general formula $$\begin{array}{c} CN \\ | \\ Ar-C=NOCH_2R^{91} \end{array}$$
(5.)

in which Ar is a phenyl or substituted phenyl radical where the substituents are optionally methyl, methoxy, chlorine, cyano or trifluoromethyl, or Ar is a naphthyl radical; $R^{91}$ is cyano,

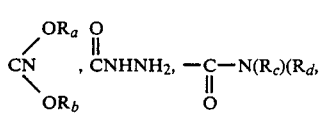

or $-CN(R_g)(R_h)$, where $R_a$ and $R_b$ are independently lower alkyl or together with the carbon form an oxygen or sulfur containing 5 or 6 membered heterocyclic ring which is unsubstituted or substituted by lower alkyl, halogen and/or nitro; ($R_c$) and ($R_d$) are independently hydrogen, lower alkyl, cycloalkyl, which are unsubsituted or further substituted with one or more halogen, lower alkoxy and/or cyano; ($R_g$) and ($R_h$) together with the nitrogen form a 5 to 6-membered ring which is unsubstituted or mono- or polysubstituted by halogen, cyano and/or lower alkyl and which can be interrupted by a nitrogen, oxygen or sulfur atom. Representative compounds of this type are those in which $R^{91}$ is cyano, and in which $R^{91}$ is 1,3-dioxolan-2-yl. The latter compound has the chemical name O-[2-(1,3-dioxolanyl)methyl]-alpha-cyanobenzaldoxime.

Thiazole carboxylic acids and derivatives suitable for use as antidotes are disclosed generally in U.S. Pat. No. 4,199,506, and have the general formula

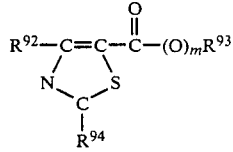
(6.)

in which $R^{92}$ is alkyl, haloalkyl or trialkoxymethyl; $R^{93}$ is variously hydrogen, agriculturally acceptable cations or various hydrocarbyl or substituted hydrocarbyl moieties; m is 0 or 1; and $R^{94}$ is chloro, bromo, iodo, lower alkoxy or substituted or unsubstituted phenoxy. A representative member of this class is the compouund benzyl-2-chloro-4-trifluoromethyl-5thiazole carboxylate ($R^{92}$=trifluoromethyl; $R^{93}$=benzyl, $R^{94}$=chloro; m=1).

Another useful herbicide antidote compound is disclosed in European Patent No. 0104495 as having the formula

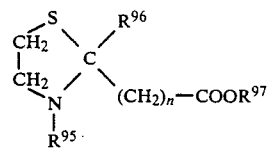

wherein $R^{95}$ represents the group

in which $R^{98}$ a $C_1-C_3$ haloalkyl containing from 1 to 3 halogen atoms or a phenyl group optionally substituted; $R^{96}$ represents a hydrogen atom, a methyl or a phenyl; $R^{97}$ represents a $C_1-C_8$ alkyl group, a $C_5-C_6$ cycloalkyl group, a cyclohexylmethyl group, a phenyl group optionally substituted, a benzyl group optionally substituted, an allyl or propargyl group; and n is zero or one.

A still further useful antidote is 1,8-naphthalic anhydride.

A representative antidote of that group would be:

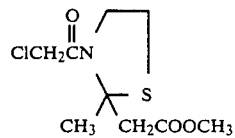

The amount of a given antidote to be utilized in combination with the herbicide composition of this invention and the manner of its utilization and resulting efficacy can vary according to various parameters, such as the particular antidote to be employed, the crop which is to be protected, the amount or rate of herbicide to be applied, the soil and climatic conditions of the agricultural environment in which the mixture is to be applied. The selection of a specific antidote for use in the herbicide composition, the manner in which it is to be applied (e.g., tank mix, in-furrow application, seed treatment, etc.), the determination of activity which is nonphytotoxic but antidotally effective, and the amount necessary to provide this result, can be readily performed utilizing the test procedures in the cited patents, such as U.S. Pat. No. 4,021,224, in accordance with common practice in the art.

For other descriptions of antidotes and methods of their use, reference is made to U.S. Pat. No. 3,959,304, Teach, May 25, 1976; U.S. Pat. No. 3,989,503, Pallos et al., Nov. 2, 1976; U.S. No. 3,131,509, Hoffman, May 5, 1964; U.S. Pat. No. 3,564,768, Hoffman, Feb. 3, 1971; U.S. Pat. No. 4,137,070, Pallos et al., Jan. 30, 1979; U.S. Pat. No. 4,294,764, Rinehart, Oct. 13, 1981; U.S. Pat. No. 4,256,481, Gardi et al., May 17, 1981; U.S. Pat. No. 4,415,353, Pallos et al., Nov. 15, 1983; and U.S. Pat. No. 4,415,352, Pallos et al., Nov. 15, 1983.

The antidote is applied in conjunction with the herbicide in a non-phytotoxic antidotally effective amount. By "non-phytotoxic" is meant an amount of the antidote which causes at most minor or no injury to the desired crop species. By "antidotally effective" is meant an antidote used in an amount which is effective as an antidote with the herbicide to decrease the extent of injury caused by the herbicide to the desired crop species. The preferred weight ratio of herbicide to antidote is from about 0.1:1 to about 30:1. Another preferred weight ratio range is from about 1:1 to about 20:1. An even more preferred weight ratio range is from about 2:1 to about 15:1.

The following examples are for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of the herbicide, the application rate of the antidote, and the ratio of the herbicide-to-antidote application, as well as the nature of crops being tested, can affect the results of the test. Results may vary from crop to crop and within the crop varieties.

ANTIDOTES:

The following antidotes were employed in Examples I, II and III and in Tables I, II, III and IV.

| | | |
|---|---|---|
| 1 | = | N,N-diallyl dichloroacetamide |
| 2 | = | 2,2,5-trimethyl-N-dichloroacetyl oxazolidine |
| 3 | = | 2,2-dimethyl-5-n-propyl-N-dichloroacetyl oxazolidine |
| I | = | α-(thiono methoxyamino)-benzacetonitrile |
| II | = | O-(2-(1,3-dioxalyl)-methyl) α-cyano benzaldoxime |
| SC | = | 2-chloro-4-(trifluoromethyl)-5-thiazole carboxylic acid benzyl ester |
| 1291 | = | N-allyl-N-(2-(1,3-dioxalanyl)methyl dichloroacetamide |
| RR | = | 2-chloro-N-isopropyl acetanilide |
| 124 | = | parachlorophenyl N-methyl carbamate |
| CDAA | = | 2-chloro-N,N-di-2-propenyl acetamide |
| TCA | = | trichloroacetic acid |
| 4 | = | 2,2-spirocyclohexyl-N-dichloroacetyl oxazolidine |
| NA | = | naphthalic anhydride |

EXAMPLE I

In a post-emergence application the following compositions were applied on 2-leaf corn compound No. 24D at 0.125 lb/A on a tank mix with antidote No. 2 at 0.125±0.15 lb/A. Corn injury with Compound No. 24D was 60–75% chlorosis and 20% stunting. The combination with No. 2 resulted in 12–20% chlorosis and 2% stunting. Also included in this test was Compound No. 8D alone at 0.75 lb/A and in a tank mix with the antidote 2 at 0.75±0.25 lb/A. Corn injury at 0.75 lb/A was 10–18% chlorosis, and 2% stunting; with No. 2, chlorosis was 2% and no stunting.

EXAMPLE II

This was a field test plot. The logarithmic spray methodology was employed, calibrated to deliver five half-lives in a strip 6.7 feet by 95 feet in dimension. This test was performed in a field plot environment. From the start to the end of the spray run, the rate of 8D and 8F was held constant at 2 lb ai/A; likewise Cmpd. 24D at 0.125 lb ai/A. For each compound, 2 was sprayed from initial rate of 0.5 lb/A to a final rate of 0.032 lg/A although 0.032 was the final rate recorded at the end of the spray run. In the table below the decrease in intensity of bleaching injury recorded in corn indicates that 8D, 8F and 24D are responsive to the antidote 2.

| Crop: Corn Weeds: Natural infestation and seeded green foxtail Degree of Bleaching | | | |
|---|---|---|---|
| Antidote | Herbicide | | |
| 2 (lb/A) | 24D (0.125 lb/A) | 8F (2 lb/A) | 8D (2 lb/A) |
| 0.500 | 0 | 10 | 5 |
| 0.250 | 0 | 60 | 15 |
| 0.125 | 5 | 85 | 15 |
| 0.063 | 20 | 93 | 40 |
| 0.032 | 25 | 98 | 60 |
| 0.000 | 43 | 98 | 98 |

The natural weeds and the seeded green foxtail were antidoted against 24D at the antidote rate within the range of 0.25 to 0.5 lb/A. No weed antidoting was noted for 8F and 8D.

EXAMPLE III

Several compounds were applied pre-emergence surface (PES) alone and with 2 to evaluate antidoting of corn, sorghum and weeds. The plots were treated with the technical herbicides and formulated antidote applied sequentially to avoid tank mix and possible incompatibility problems, if either should exist. Trial design was randomized complete block using two replications, and the soil was a sandy loam with 2.3% organic matter. The front ¾ of each plot was planted to one row each of corn (*Zea mays*), cv. DeKalb XL-6060, and grain sorghum (*Sorghum bicolor*), cv. Funk's G-251. Seeded across the back quarter were johnsongrass (*Sorghum halepense*), green foxtail (*Setaria viridis*), giant foxtail (*Setaria faberi*), annual morningglory (*Ipomoea purpurea*), and sicklepod (*Casia*). Warm days and cool nights prevailed during the first two weeks after application, approximating spring-like conditions. The complete treatment list and initial corn and weed ratings are presented in the table below.

Sorghum showed almost total necrosis with all herbicides and no response to the antidote. Good protection from chlorosis and stunting resulted in corn with all compounds, although 2 appeared to contribute to stunting in the 51A and 4D treatments. Stand count in this field test was not uniform due to bird feeding. However, this did not influence eealuation of the antidoting effect and subsequent rating. Some minor weed antidoting occurred.

| Compounds and Formulation | Rates (lb ai/A) | Mean Percent Corn Tolerance and Weed Control 2 Weeks After Treatment ||||||||||||||
|---|---|---|---|---|---|---|---|---|---|---|---|---|---|---|---|
| | | Corn Tolerance ||| Johnson-grass || Green foxtail || Giant foxtail || Annual Morning-glory || Sicklepod ||
| | | 1 | 2 | 3 | CONT | SUPP | CONT | SUPP | CONT | SUPP | CONT | SUPP | CONT | SUPP |
| 51A T | 1.50 | 25 | 10 | 8 | 62 | 92 | 100 | 100 | 74 | 88 | 97 | 99 | 50 | 96 |
| 4D T | 1.00 | 16 | 10 | 5 | 84 | 97 | 100 | 100 | 93 | 99 | 41 | 68 | 17 | 85 |
| 8D T | 1.00 | 81 | 40 | 23 | 60 | 95 | 99 | 93 | 100 | 100 | 100 | 100 | 92 | 99 |
| 24D T | 0.25 | 79 | 75 | 35 | 97 | 99 | 100 | 100 | 93 | 99 | 97 | 99 | 50 | 99 |
| 51A T + 2 | 1.50 + 0.25 | 7 | 8 | 15 | 63 | 88 | 100 | 100 | 66 | 91 | 100 | 100 | 17 | 96 |
| 4D T + 2 | 1.00 + 0.25 | 2 | 3 | 10 | 72 | 96 | 100 | 100 | 95 | 99 | 72 | 90 | 0 | 88 |
| 8D T + 2 | 1.00 + 0.25 | 7 | 5 | 15 | 42 | 91 | 100 | 100 | 100 | 100 | 100 | 100 | 92 | 98 |
| 24D T + 2 | 0.25 + 0.25 | 13 | 8 | 13 | 83 | 97 | 100 | 100 | 93 | 98 | 94 | 98 | 9 | 96 |
| CONTROL | | 4 | 5 | 0 | 0 | 0 | 0 | 0 | 0 | 0 | 0 | 0 | 0 | 0 |

CONT = Control, SUPP = Suppression.
1 = Incidence of chlorosis
2 = Severity of chlorosis
3 = Stunting
T = Technical Material

EXAMPLE IV

SEED TREATMENT

Various combinations of herbicides and antidote were evaluated for protection of corn and sorghum against herbicide injury in a PES trial. Soil type was a sandy loam having 2.3% organic matter. Herbicide treatments were arranged in a randomized complete block design with two replications. The front ¾ of each herbicide plot was planted to four rows each of corn (zea mays), c.v. DeKalb XL-6060, and grain sorghum (Sorghum bicolor), cv. Funk's G 251. These rows consisted of no seed treatment and seed treatments of 1, 2 and 3. Across the back ¼ of the plots were seeded johnsongrass (Sorghum halapense), green foxtail (Setaria viridis), giant foxtail (Setaria faberi), annual morningglory (Ipomoea purpurea), and sicklepod (Cassia). Favorable weather occurred the first two weeks after application, consisting of warm days and cool nights. Treatment combinations and initial corn and weed ratings are given in the following table.

Sorghum necrosis approached 100% in all treatments. Differences in corn stands between seed treatments resulted primarily from non-uniform planting depths from row to row. The herbicide/antidote combinations appeared to have little effect on corn stand. Protection against chlorosis varied by herbicide and by antidote.

Results hereinafter are reported as a fraction as follows:

$$\left[ \frac{\% \text{ injury with antidote}}{\% \text{ injury without antidote}} \right]$$

| Compounds & Formulation | Rates (lb ai/A + ai/W %) | Mean Percent Corn Tolerance and Weed Control 2 Weeks After Treatment |||||
|---|---|---|---|---|---|---|
| | | Corn Tolerance || Johnson-grass || Green foxtail ||
| | | 1 | 2 | CONT | SUPP | CONT | SUPP |
| 51A T | 1.50 | 20 | 18 | 73 | 97 | 100 | 100 |
| 51A T + 1 2E | 1.50 + 0.50% | 0 | 0 | 73/73 | 97/97 | 100/100 | 100/100 |
| 51A T + 2 2E | 1.50 + 0.25% | 0 | 0 | 73/73 | 97/97 | 100/100 | 100/100 |
| 51A T + 2 2E | 1.50 + 0.50% | 0 | 0 | 73/73 | 97/97 | 100/100 | 100/100 |
| 4D T | 1.00 | 18 | 18 | 74 | 98 | 100 | 100 |
| 4D T + 1 6E | 1.00 + 0.50% | 0 | 0 | 74/74 | 98/98 | 100/100 | 100/100 |
| 4D T + 2 2E | 1.00 + 0.25% | 0 | 0 | 74/74 | 98/98 | 100/100 | 100/100 |
| 4D T + 3 50/ST* | 1.00 + 0.50% | 0 | 0 | 74/74 | 98/98 | 100/100 | 100/100 |
| 8D T | 1.00 | 91 | 38 | 47 | 95 | 100 | 100 |
| 8D T + 1 6E | 1.00 + 0.50% | 5 | 8 | 47/47 | 95/95 | 100/100 | 100/100 |
| 8D T + 2 2E | 1.00 + 0.25% | 0 | 0 | 47/47 | 95/95 | 100/100 | 100/100 |
| 8D T + 3 50/ST* | 1.00 + 0.50% | 0 | 0 | 47/47 | 95/95 | 100/100 | 100/100 |
| 24D T | 0.25 | 100 | 75 | 95 | 99 | 99 | 99 |
| 24D T + 1 6E | 0.25 + 0.50% | 47 | 25 | 95/95 | 99/99 | 99/99 | 99/99 |
| 24D T + 2 2E | 0.25 + 0.25% | 0 | 0 | 95/95 | 99/99 | 99/99 | 99/99 |
| 24D T + 3 50/ST* | 0.25 + 0.50% | 47 | 28 | 95/95 | 99/99 | 99/99 | 99/99 |
| 1 6E | 0.50% | 0 | 0 | 0 | 0 | 0 | 0 |
| 2 2E | 0.25% | 0 | 0 | 0 | 0 | 0 | 0 |
| 3 50/ST | 0.50% | 0 | 0 | 0 | 0 | 0 | 0 |
| CONTROL | | 1 | 3 | 0 | 0 | 0 | 0 |

| Compounds & Formulation | Rates (lb ai/A + ai/W %) | Giant foxtail | Annual Morning-glory || Sicklepod ||
|---|---|---|---|---|---|---|
| | | CONT | CONT | SUPP | CONT | SUPP |
| 51A T | 1.50 | 100 | 100 | 100 | 94 | 95 |
| 51A T + 1 2E | 1.50 + 0.50% | 100/100 | 100/100 | 100/100 | 94/94 | 100/95 |
| 51A T + 2 2E | 1.50 + 0.25% | 100/100 | 100/100 | 100/100 | 94/94 | 100/95 |
| 51A T + 2 2E | 1.50 + 0.50% | 100/100 | 100/100 | 100/100 | 94/94 | 100/95 |
| 4D T | 1.00 | 100 | 22 | 70 | 57 | 85 |
| 4D T + 1 6E | 1.00 + 0.50% | 100/100 | 22/22 | 70/70 | 57/57 | 85/85 |

-continued
Mean Percent Corn Tolerance and Weed Control 2 Weeks After Treatment

| | | | | | | | |
|---|---|---|---|---|---|---|---|
| 4D T + 2 2E | 1.00 + | 0.25% | 100/100 | 22/22 | 70/70 | 57/57 | 85/85 |
| 4D T + 3 50/ST* | 1.00 + | 0.50% | 100/100 | 22/22 | 70/70 | 57/57 | 85/85 |
| 8D T | 1.00 | | 100 | 100 | 100 | 92 | 99 |
| 8D T + 1 6E | 1.00 + | 0.50% | 100/100 | 100/100 | 100/100 | 92/57 | 99/99 |
| 8D T + 2 2E | 1.00 + | 0.25% | 100/100 | 100/100 | 100/100 | 92/57 | 99/99 |
| 8D T + 3 50/ST* | 1.00 + | 0.50% | 100/100 | 100/100 | 100/100 | 92/57 | 99/99 |
| 24D T | 0.25 | | 100 | 93/93 | 99 | 79 | 93 |
| 24D T + 1 6E | 0.25 + | 0.50% | 100/100 | 93/93 | 99/99 | 79/79 | 93/93 |
| 24D T + 2 2E | 0.25 + | 0.25% | 100/100 | 93/93 | 99/99 | 79/79 | 93/93 |
| 24D T + 3 50/ST* | 0.25 + | 0.50% | 100/100 | 93/93 | 99/99 | 79/79 | 93/93 |
| 1 6E | | 0.50% | 0 | 0 | 0 | 0 | 0 |
| 2 2E | | 0.25% | 0 | 0 | 0 | 0 | 0 |
| 3 50/ST | | 0.50% | 0 | 0 | 0 | 0 | 0 |
| CONTROL | | | 0 | 0 | 0 | 0 | 0 |

*Seed treatment powdered formulation.
CONT = control; SUPP = suppression.
1 = Incidence of chlorosis.
2 = Severity of chlorosis.
T = Technical Material
2E and 6E represent formulations which contain 2 and 6 lbs/gal and an emulsifier.

TESTS
TABLES I, II, III, IV

Condition of test: Tank Mix and Seed Treatment
Soil Type: Sandy Loam
Method of application and procedure:
  Pre-emergence surface applied as tank mix (PES-TM); or
  Seed treatment 10 grams of seeds treated with antidote
Compound at various weight percents as indicated.
Ratings as indicated.
Seedings:  Crop:  Corn 25A - CN 25A
              Corn 55A - CN 55A
              Corn XL-379 - CN XL-379
              Corn XL-67 - CN XL-67
              Corn XL-71 - CN XL-71
              Corn Funks G-4315 - CN G-4315
              Corn XL-447 - CN XL-447
              Corn XL-23A - CN XL-23A
              Corn Pioneer 3475 - CN 3475
              Corn Sweet - CN Sweet
         Weed:  Yellow Nutsedge - YNS
              Green Foxtail - GFT
              Watergrass - WG
              Shattercane - SHC The herbicide was surface applied preemergence to the planted treated seed. The emerged plants were rated 3 weeks after treatment. The plants were compared to plants which had not received treatments.

TABLE I

| Treatment Herbicide + Antidote | PES Tank Mix Rated 26 Days | | | |
|---|---|---|---|---|
| | Rate* lb/A | XL-55 | FUNKS | WG |
| 4D + 1 | 1 + 2 | 8/35 | 38/40 | 99/95 |
| | 1 + 1 | 10/35 | 30/40 | 99/95 |
| 4D + 2 | 1 + 2 | 25/35 | 25/40 | 99/95 |

*Herbicide + Antidote

TABLE II

| Treatment: Herbicide + Antidote | Rate* lb/A | PES Tank Mix Antidote Test Rated 3 weeks | | | | | |
|---|---|---|---|---|---|---|---|
| | | CN 25A | CN 55A | CN XL-379 | YNS | CN G-4315 | CN XL-71 |
| 4D + 1 | 1 + 0.5 | 3/38 | 8/65 | — | 85/87 | 18/60 | 10/60 |
| | 1 + 1 | 10/38 | 18/65 | — | 85/87 | 25/60 | 35/60 |
| | 1 + 2 | 10/38 | 15/65 | — | 85/87 | 15/60 | 0/60 |
| 4D + 2 | 1 + 0.5 | 7/38 | 13/65 | — | 85/87 | 15/60 | 8/60 |
| | 1 + 1 | 3/38 | 10/65 | — | 85/87 | 18/60 | 10/60 |
| | 1 + 2 | 3/38 | 5/65 | — | 90/87 | 10/60 | 5/60 |
| 51A + 1 | 1 + 0.5 | 3/3 | 0/3 | 25/15 | 90/90 | 3/10 | 5/13 |
| | 1 + 1 | 0/3 | 0/3 | 25/15 | 90/90 | 3/10 | 8/13 |
| | 1 + 2 | 0/3 | 0/3 | — | 90/90 | 5/10 | 5/13 |
| 51A + 2 | 1 + 0.5 | 3/3 | 0/3 | — | 90/90 | 3/10 | 8/13 |
| | 1 + 1 | 0/3 | 0/3 | 0/15 | 90/90 | 5/10 | 3/13 |
| | 1 + 2 | 0/3 | 3/3 | 0/15 | 90/90 | 3/10 | 5/13 |

TABLE III

| Treatment: Herbicide + Antidote | Rate* lb/A | Seed Treatment (10 g seeds/5 mg antidote: 0.05% by w/w) Rated 3 weeks | | | | | |
|---|---|---|---|---|---|---|---|
| | | CN 25A | CN 55A | CN XL-379 | YNS | CN G-4315 | CN XL-71 |
| 4D + 1 | 0.5 | 0/5 | 0/20 | 0/40 | 83/85 | 40/20 | 20/15 |
| | 1 | 20/38 | 45/65 | — | 85/87 | 60/60 | 45/60 |
| 4D + 2 | 0.5 | 0/5 | 3/20 | 5/40 | 85/85 | 3/20 | 0/15 |
| | 1 | 3/38 | 0/65 | — | 87/87 | 25/60 | 18/60 |

TABLE III-continued

Seed Treatment (10 g seeds/5 mg antidote: 0.05% by w/w)
Rated 3 weeks

| Treatment: Herbicide + Antidote | Rate* lb/A | CN 25A | CN 55A | CN XL-379 | YNS | CN G-4315 | CN XL-71 |
|---|---|---|---|---|---|---|---|
| 51A + | 1 | 5/3 | 3/3 | — | 90/90 | 40/10 | 13/13 |
| 1 | 2 | 20/25 | 20/50 | — | 90/95 | 65/50 | 65/28 |
| 51A + | 1 | 3/3 | 0/3 | — | 90/90 | 5/10 | 3/13 |
| 2 | 2 | 25/25 | 0/50 | — | 90/95 | 18/50 | 15/28 |

*Herbicide + Antidote

TABLE IV

PES Tank mix (25 gal/A)
Rated 16 days

| Treatment | Herb. + Ant. Rate lb/A | GFT | CN XL-55 | CN XL-447 | CN XL-23A | CN 3475 |
|---|---|---|---|---|---|---|
| 4D + | 0.5 + 0.5 | 100/100 | 5/40 | 0/35 | 0/35 | 0/20 |
| 2 | 0.5 + 1 | 100/100 | 0/40 | 0/35 | 0/35 | 0/20 |
| 4D + | 0.5 + 0.5 | 100/100 | 0/40 | 10/35 | 10/35 | 10/20 |
| 1 | 0.5 + 1 | 100/100 | 10/40 | 10/35 | 10/35 | 0/20 |
|  | 0.5 + 2 | 100/100 | 0/40 | 0/35 | 0/35 | 0/20 |
| 4D + | 0.5 + 0.125 | 100/100 | 20/40 | 20/35 | 40/35 | 50/20 |
| I | 0.5 + 0.25 | 100/100 | 40/40 | 40/35 | 45/35 | 45/20 |
|  | 0.5 + 0.5 | 100/100 | 40/40 | 10/35 | 25/35 | 40/20 |
| 4D + | 0.5 + 0.125 | 100/100 | 55/40 | 45/35 | 50/35 | 50/20 |
| II | 0.5 + 0.25 | 100/100 | 60/40 | 55/35 | 55/35 | 60/20 |
|  | 0.5 + 0.5 | 100/100 | 30/40 | 35/35 | 35/35 | 30/20 |
| 4D + | 0.5 + 0.125 | 100/100 | 15/40 | 15/35 | 30/35 | 15/20 |
| SC | 0.5 + .25 | 100/100 | 45/40 | 15/35 | 25/35 | 25/20 |
|  | 0.5 + 0.5 | 100/100 | 35/40 | 10/35 | 10/35 | 20/20 |
| 4D + | 0.5 + 0.5 | 100/100 | 45/40 | 20/35 | 30/35 | 25/20 |
| 4 | 0.5 + 1 | 100/100 | 30/40 | 25/35 | 25/35 | 30/20 |
| 4D + | 0.5 + 0.125 | 100/100 | 45/40 | 30/35 | 45/35 | 50/20 |
| 124 | 0.5 + 0.25 | 100/100 | 55/40 | 50/35 | 50/35 | 60/20 |
| 4D + | 0.5 + 0.5 | 100/100 | 5/40 | 15/35 | 30/35 | 20/20 |
| 1292 | 0.5 + 1 | 100/100 | 0/40 | 0/35 | 15/35 | 10/20 |
| 4D + | 0.5 + 0.125 | 100/100 | 55/40 | 35/35 | 45/35 | 45/20 |
| NA | 0.5 + 0.25 | 100/100 | 45/40 | 45/35 | 45/35 | 40/20 |
|  | 0.5 + 0.5 | 100/100 | 25/40 | 10/35 | 25/35 | 15/20 |
| 4D + | 0.5 + 0.5 | 100/100 | 15/40 | 15/35 | 0/35 | 0/20 |
| 3 | 0.5 + 1 | 100/100 | 15/40 | 10/35 | 0/35 | 15/20 |
|  | 0.5 + 2 | 100/100 | 5/40 | 0/35 | 10/35 | 15/20 |
| 4D + | 0.5 + 0.125 | 100/100 | 25/40 | 40/35 | 40/35 | 50/20 |
| RR | 0.5 + 0.25 | 100/100 | 55/40 | 35/35 | 30/35 | 35/20 |
|  | 0.5 + 0.5 | 100/100 | 45/40 | 25/35 | 35/35 | 40/20 |
| 4D + CDAA | 0.5 + 0.125 | 100/100 | 35/40 | 40/35 | 45/35 | 35/35 |
|  | 0.5 + 0.25 | 100/100 | 40/40 | 40/35 | 45/35 | 30/35 |
|  | 0.5 + 0.5 | 100/100 | 55/40 | 55/35 | 45/35 | 35/35 |
| 4D + TCA | 0.5 + 0.125 | 100/100 | 60/40 | 30/35 | 35/35 | 30/20 |
|  | 0.5 + 0.25 | 100/100 | 60/40 | 45/35 | 45/35 | 35/20 |
|  | 0.5 + 0.5 | 100/100 | 50/40 | 40/35 | 65/35 | 60/20 |

TABLE IVA

| Application | PES Tank Mix (25 gal/A) |
|---|---|
| Soil | Sandy loam |
| Flats | 9" × 6" × 4" aluminum flats |
| Rated | 23 days after treatment |
| Seeding | SETVI (green foxtail), XL-55A corn, XL-23A corn, Pioneer 3475 corn |

| Treatment | Rate (lb/A) | SETVI | CN XL-55A | CN XL-23A | CN3475 |
|---|---|---|---|---|---|
| 4D | 0.5 | 100 | 15 | 30 | 45 |
| 4D + | 0.5 + 0.5 | 100/100 | 5/15 | 5/30 | 5/45 |
| 2 | 0.5 + 1.0 | 100/100 | 0/15 | 5/30 | 5/45 |
| 4D + | 0.5 + 0.5 | 100/100 | 10/15 | 15/30 | 10/45 |
| 1 | 0.5 + 1.0 | 100/100 | 25/15 | 15/30 | 0/45 |
| 4D + | 0.5 + 0.5 | 100/100 | 5/15 | 10/30 | 20/45 |
| 3 | 0.5 + 1.0 | 100/100 | 5/15 | 5/30 | 5/45 |
| 4D + | 0.5 + 0.125 | 100/100 | 25/15 | 30/30 | 20/45 |
| I | 0.5 + 1.0 | 100/100 | 15/15 | 25/25 | 25/45 |
| 4D + | 0.5 + 0.125 | 100/100 | 20/15 | 30/30 | 29/45 |
| II | 0.5 + 1.0 | 100/100 | 35/15 | 25/30 | 25/45 |
| 4D + | 0.5 + 0.125 | 100/100 | 20/15 | 20/30 | 25/45 |
| SC | 0.5 + 0.25 | 100/100 | 5/15 | 20/30 | 15/45 |
| 4D + | 0.5 + 0.5 | 100/100 | 20/15 | 15/30 | 45/45 |
| 4 | 0.5 + 1.0 | 100/100 | 20/15 | 25/30 | 25/45 |
| 4D + | 0.5 + 0.125 | 100/100 | 30/15 | 50/30 | 65/45 |
| 124 | 0.5 + 0.25 | 100/100 | 40/15 | 65/30 | 70/45 |
| 4D + | 0.5 + 0.5 | 100/100 | 20/15 | 15/30 | 0/45 |
| 1292 | 0.5 + 1.0 | 100/100 | 15/15 | 15/30 | 0/45 |
| 4D + | 0.5 + 0.5 | 100/100 | 60/15 | 60/30 | 60/45 |
| NA | 0.5 + 1.0 | 100/100 | 30/15 | 25/30 | 0/45 |
| 4D + | 0.5 + 0.5 | 100/100 | 60/15 | 60/30 | 60/45 |
| RR | 0.5 + 1.0 | 100/100 | 20/15 | 70/30 | 80/45 |
| 4D + | 0.5 + 0.5 | 100/100 | 30/15 | 60/30 | 45/45 |
| CDAA | 0.5 + 1.0 | 100/100 | 65/15 | 60/30 | 35/45 |
| 4D + | 0.5 + 0.5 | 100/100 | 50/15 | 60/30 | 40/45 |
| TCA | 0.5 + 1.0 | 100/100 | 40/15 | 25/30 | 30/45 |
| Con- | — | 0 | 0 | 0 | 0 |

TABLE IVA-continued

| | | | CN | CN | |
|---|---|---|---|---|---|
| Application | PES Tank Mix (25 gal/A) | | | | |
| Soil | Sandy loam | | | | |
| Flats | 9" × 6" × 4" aluminum flats | | | | |
| Rated | 23 days after treatment | | | | |
| Seeding | SETVI (green foxtail), XL-55A corn, XL-23A corn, Pioneer 3475 corn | | | | |
| Treatment | Rate (lb/A) | SETVI | XL-55A | XL-23A | CN3475 |
| trol | | 0 | 0 | 0 | 0 |

TABLES V, V-A, V-B

MATERIAL AND METHODS

The following herbicide/antidote tests were conducted with various plant species. The corn hybrids and weed species employed in each test for Tables V, V-A and V-B are as follows:

AMARE—*Amaranthus retroflexus*—(redroot pigweed)
SETVI—*Setaria viridis*—(green foxtail)
ECHCG—*Echinochloa crusgalli*—(watergrass)
Corn—DeKalb XL64; DeKalb XL-23A; Pioneer 3475.

Herbicide compounds and antidotes employed in the tests were sprayed in an acetone-water solution containing polyoxyethylene sorbitan monolaurate emulsifier. Herbicides and antidotes were applied as preemergence tank mix solution (PES) with a cover volume of 25 gal/A. All seeds were seeded in aluminum flats (16×23×7 cm) of which holes were punched in the bottom to allow water drainage. Seeds were planted 3 cm deep, except that AMARE (*Amaranthus retroflexus*), which was planted 1.5 cm deep, in a sandy loam soil fortified with fertilizer (17-17-17; Garden Valley Fertilizer Co., San Jose, CA 95112) and the fungicide Captan 80W. All compounds were applied preemergence tank mix and all compounds were applied with linear spray table.

After treatment, all flats were placed into a greenhouse. Greenhouses were maintained at about 25° C. and 20° C., day and night temperatures, respectively. All flats were watered with overhead sprinkling. After treatment visual ratings of weed control and crop injury were recorded. Ratings were stated as percentage of control or injury of each individual species as compared with an untreated control. The injury ratings range from 0 to 100%, where 0 represents no effect on growth and 100 represents complete kill.

TABLES V, V-A, V-B

The following compounds were employed as examples of antidotes in Tables V, V-A, and V-B.

| | |
|---|---|
| 1 | N,N-diallyl dichloroacetamide |
| 5 | 2,2-bis-(ethylthio)N,N-diallylacetamide |
| 6 | 2,2-dichloro-N-ethyl-N-benzyl acetamide |
| 7 | 2,2-dimethyl-3-dichloroacetyl oxazolidine |
| 2 | 2,2,5-trimethyl-N-dichloroacetyl oxazolidine |
| 8 | 2-methyl-2-ethyl-N-dichloroacetyl oxazolidine |
| 4 | 2,2-spirocyclohexyl-N-dichloroacetyl oxazolidine |
| 9 | 2,2-dimethyl-N-dichloroacetyl thiazolidine |
| 10 | 2-propyl-3-dichloroacetyl oxazolidine |
| 11 | 2,5-dimethyl-3-dichloroacetyl oxazolidine |
| 12 | 2-methyl-2-isopropyl-3-dichloroacetyl oxazolidine |
| 13 | N-t-butyl-2,3-dibromopropionamide |
| 14 | 2,2,4-trimethyl(3-dichloroacetyl)-1,3-oxazolidine |
| 15 | N-t-pentyl 2,3-dibromopropionamide |
| 16 | 2,2,4-trimethyl-3-dichloroacetyl oxazolidine |
| 17 | 2,2,5,5-tetramethyl-3-dichloroacetyl oxazolidine |
| 18 | 2,2-dimethyl-3-dichloroacetyl-5-propyl oxazolidine |
| 19 | 3-dichloroacetyl-2,2,5-trimethyl thiazolidine |
| 20 | 2,2,4,5-tetramethyl-3-dichloroacetyl oxazolidine |
| 21 | N-(dimethyl-2-butynyl)-2,3-dibromopropionamide |
| 22 | 2,2-dimethyl-N-dichloroacetyl-5-ethyl oxazolidine |
| 23 | 2,5-dimethyl-2-ethyl-3-dichloroacetyl oxazolidine |
| 24 | 2,2-dimethyl-3-dichloroacetyl-5-butyl oxazolidine |
| 25 | 2,2-dimethyl-3-dichloroacetyl-5-methoxymethyl oxazolidine |
| 26 | 2,2-dimethyl-3-dichloroacetyl-5-ethoxymethyl oxazolidine |
| 27 | 2,2-dimethyl-3-dichloroacetyl-4,5-tetramethylene oxazolidine |
| 28 | 2,2-dimethyl-3-dichloroacetyl-4,5-trimethylene oxazolidine |
| 29 | 2,2-dimethyl-3-dichloroacetyl-5-ethyl-thiomethyl oxazolidine |
| 30 | N-dichloroacetyl-2-trichloromethyl-5-methyl oxazolidine |
| 31 | 2,2,5-trimethyl-3-hydroxyacetyl oxazolidine |
| 32 | 2-methyl-2-dichloromethyl-1,3-dioxolane |

TABLE V

| Treatment | Rate kg/ha Herb + Ant. | AMARE | SETVI | ECHCG | CN 64 | CN23A | CN3475 |
|---|---|---|---|---|---|---|---|
| | | RATING 3 WEEKS AFTER TREATMENT | | | | | |
| 24D + 2 | 0.28 + 0.07 | 93/98 | 100/88 | 95/100 | 30/50 | 45/55 | 70/58 |
| 24D + 2 | 0.28 + 0.14 | 100/98 | 100/88 | 100/100 | 33/50 | 60/55 | 63/58 |
| 24D + 2 | 0.28 + 0.28 | 100/98 | 90/88 | 100/100 | 23/50 | 13/55 | 43/55 |
| 24D + 2 | 0.28 + 0.56 | 95/98 | 98/88 | 100/100 | 38/50 | 48/55 | 53/58 |
| 24D + 7 | 0.28 + 0.14 | 95/98 | 100/88 | 100/100 | 78/50 | 60/55 | 68/58 |
| 24D + 7 | 0.28 + 0.28 | 100/98 | 100/88 | 100/100 | 35/50 | 40/55 | 60/58 |
| 24D + 7 | 0.28 + 0.56 | 95/98 | 100/88 | 100/100 | 35/50 | 28/55 | 58/58 |
| 24D + 9 | 0.28 + 0.14 | 100/98 | 100/88 | 100/100 | 25/50 | 43/55 | 68/58 |
| 24D + 9 | 0.28 + 0.28 | 100/98 | 98/88 | 100/100 | 35/50 | 53/55 | 63/58 |
| 24D + 9 | 0.28 + 0.56 | 98/98 | 95/88 | 100/100 | 40/50 | 35/55 | 38/58 |
| 24D + 6 | 0.28 + 0.14 | 100/98 | 100/88 | 100/100 | 50/50 | 85/55 | 85/58 |
| 24D + 6 | 0.28 + 0.28 | 100/98 | 100/88 | 100/100 | 38/50 | 50/55 | 53/58 |
| 24D + 6 | 0.28 + 0.56 | 100/98 | 100/88 | 100/100 | 58/50 | 50/55 | 60/58 |
| 24D + | 0.28 + | 100/98 | 100/88 | 100/100 | 35/50 | 30/55 | 40/55 |

TABLE V-continued

| Treatment | Rate kg/ha Herb + Ant. | AMARE | SETVI | ECHCG | CN 64 | CN23A | CN3475 |
|---|---|---|---|---|---|---|---|
| 4 | 0.14 | | | | | | |
| 24D + 4 | 0.28 + 0.28 | 98/98 | 100/88 | 100/100 | 80/50 | 80/55 | 70/58 |
| 24D + 4 | 0.28 + 0.56 | 100/98 | 100/88 | 100/100 | 50/50 | 60/55 | 55/58 |
| 24D + 1 | 0.28 + 0.14 | 100/98 | 100/88 | 100/100 | 83/50 | 65/55 | 63/58 |
| 24D + 1 | 0.28 + 0.28 | 99/98 | 100/88 | 100/100 | 65/50 | 70/55 | 53/58 |
| 24D + 1 | 0.28 + 0.56 | 98/98 | 95/88 | 100/100 | 38/50 | 50/55 | 53/58 |
| 24D + 2 | 0.56 + 0.07 | 100/100 | 100/100 | 100/100 | 70/85 | 63/88 | 43/80 |
| 24D + 2 | 0.56 + 0.14 | 100/100 | 100/100 | 100/100 | 80/85 | 78/88 | 70/80 |
| 24D + 2 | 0.56 + 0.28 | 100/100 | 100/100 | 100/100 | 75/85 | 78/88 | 75/80 |
| 24D + 2 | 0.56 + 0.56 | 98/100 | 100/100 | 100/100 | 63/85 | 68/88 | 60/80 |
| 24D + 7 | 0.56 + 0.14 | 98/100 | 100/100 | 100/100 | 68/85 | 75/88 | 65/80 |
| 24D + 7 | 0.56 + 0.28 | 100/100 | 100/100 | 100/100 | 60/85 | 80/88 | 85/80 |
| 24D + 7 | 0.56 + 0.56 | 100/100 | 100/100 | 100/100 | 58/85 | 68/88 | 78/80 |
| 24D + 9 | 0.56 + 0.14 | 98/100 | 100/100 | 100/100 | 60/85 | 73/88 | 78/80 |
| 24D + 9 | 0.56 + 0.28 | 85/100 | 95/100 | 100/100 | 58/85 | 75/88 | 65/80 |
| 24D + 9 | 0.56 + 0.56 | 98/100 | 100/100 | 100/100 | 65/85 | 78/88 | 75/80 |
| 24D + 6 | 0.56 + 0.14 | 100/100 | 100/100 | 100/100 | 80/85 | 80/88 | 78/80 |
| 24D + 6 | 0.56 + 0.28 | 98/100 | 100/100 | 100/100 | 90/85 | 88/88 | 85/80 |
| 24D + 6 | 0.56 + 0.56 | 100/100 | 100/100 | 100/100 | 85/85 | 78/88 | 73/80 |
| 24D + 4 | 0.56 + 0.14 | 100/100 | 100/100 | 100/100 | 80/85 | 85/88 | 83/80 |
| 24D + 4 | 0.56 + 0.28 | 98/100 | 100/100 | 100/100 | 75/85 | 70/88 | 88/80 |
| 24D + 4 | 0.56 + 0.56 | 100/100 | 100/100 | 100/100 | 98/85 | 95/88 | 73/80 |
| 24D + 1 | 0.56 + 0.14 | 100/100 | 100/100 | 100/100 | 75/85 | 83/88 | 75/80 |
| 24D + 1 | 0.56 + 0.28 | 100/100 | 100/100 | 100/100 | 63/85 | 90/88 | 95/80 |
| 24D + 1 | 0.56 + 0.56 | 100/100 | 100/100 | 100/100 | 68/85 | 80/88 | 80/80 |
| 4D + 2 | 0.56 + 0.07 | 93/97 | 100/100 | 100/100 | 15/15 | 0/15 | 13/23 |
| 4D + 2 | 0.56 + 0.14 | 63/97 | 100/100 | 100/100 | 10/15 | 15/15 | 20/23 |
| 4D + 2 | 0.56 + 0.28 | 78/97 | 100/100 | 100/100 | 20/15 | 15/15 | 20/23 |
| 4D + 2 | 0.56 + 0.56 | 83/97 | 100/100 | 100/100 | 15/15 | 20/15 | 20/23 |
| 4D + 7 | 0.56 + 0.14 | 65/97 | 100/100 | 100/100 | 8/15 | 10/15 | 15/23 |
| 4D + 7 | 0.56 + 0.28 | 83/97 | 100/100 | 100/100 | 25/15 | 20/15 | 20/23 |
| 4D + 7 | 0.56 + 0.56 | 75/97 | 100/100 | 100/100 | 0/15 | 13/15 | 8/23 |
| 4D + 9 | 0.56 + 0.14 | 50/97 | 98/100 | 100/100 | 0/15 | 8/15 | 0/23 |
| 4D + 9 | 0.56 + 0.28 | 35/97 | 100/100 | 100/100 | 0/15 | 0/15 | 8/23 |
| 4D + 9 | 0.56 + 0.56 | 98/97 | 100/100 | 100/100 | 0/15 | 8/15 | 5/23 |
| 4D + 6 | 0.56 + 0.14 | 70/97 | 100/100 | 100/100 | 10/15 | 8/15 | 8/23 |
| 4D + 6 | 0.56 + 0.28 | 75/97 | 100/100 | 100/100 | 3/15 | 0/15 | 5/23 |
| 4D + 6 | 0.56 + 0.56 | 75/97 | 100/100 | 100/100 | 5/15 | 0/15 | 5/23 |
| 4D + 4 | 0.56 + 0.14 | 88/97 | 100/100 | 100/100 | 20/15 | 5/15 | 8/23 |
| 4D + 4 | 0.56 + 0.28 | 75/97 | 100/100 | 100/100 | 13/15 | 5/15 | 5/23 |

TABLE V-continued

| Treatment | Rate kg/ha Herb + Ant. | AMARE | SETVI | ECHCG | CN 64 | CN23A | CN3475 |
|---|---|---|---|---|---|---|---|
| 4D + 4 | 0.56 + 0.56 | 98/97 | 100/100 | 100/100 | 15/15 | 13/15 | 15/23 |
| 4D + 1 | 0.56 + 0.14 | 63/97 | 100/100 | 100/100 | 20/15 | 0/15 | 8/23 |
| 4D + 1 | 0.56 + 0.28 | 50/97 | 100/100 | 100/100 | 13/15 | 5/15 | 5/23 |
| 4D + 1 | 0.56 + 0.56 | 78/97 | 100/100 | 100/100 | 5/15 | 15/15 | 10/23 |
| 4D + 2 | 1.12 + 0.07 | 98/65 | 100/100 | 100/100 | 5/13 | 15/25 | 8/25 |
| 4D + 2 | 1.12 + 0.14 | 98/65 | 100/100 | 100/100 | 30/13 | 13/25 | 10/25 |
| 4D + 2 | 1.12 + 0.28 | 85/65 | 100/100 | 100/100 | 5/13 | 10/25 | 13/25 |
| 4D + 2 | 1.12 + 0.56 | 58/65 | 100/100 | 100/100 | 18/13 | 20/25 | 13/25 |
| 4D + 7 | 1.12 + 0.14 | 48/65 | 100/100 | 100/100 | 18/13 | 15/25 | 15/25 |
| 4D + 7 | 1.12 + 0.28 | 100/65 | 100/100 | 100/100 | 18/13 | 5/25 | 13/25 |
| 4D + 7 | 1.12 + 0.56 | 60/65 | 100/100 | 100/100 | 23/13 | 30/25 | 30/25 |
| 4D + 9 | 1.12 + 0.14 | 63/65 | 100/100 | 100/100 | 20/13 | 18/25 | 18/25 |
| 4D + 9 | 1.12 + 0.28 | 100/65 | 100/100 | 100/100 | 30/13 | 15/25 | 10/25 |
| 4D + 9 | 1.12 + 0.56 | 65/65 | 100/100 | 100/100 | 10/13 | 15/25 | 15/25 |
| 4D + 6 | 1.12 + 0.14 | 93/65 | 100/100 | 100/100 | 20/13 | 18/25 | 20/25 |
| 4D + 6 | 1.12 + 0.28 | 93/65 | 100/100 | 100/100 | 13/13 | 20/25 | 18/25 |
| 4D + 6 | 1.12 + 0.56 | 58/65 | 80/100 | 98/100 | 8/13 | 18/25 | 8/25 |
| 4D + 4 | 1.12 + 0.14 | 68/65 | 100/100 | 100/100 | 20/13 | 20/25 | 45/25 |
| 4D + 4 | 1.12 + 0.28 | 100/65 | 100/100 | 100/100 | 50/13 | 28/25 | 33/25 |
| 4D + 4 | 1.12 + 0.56 | 58/65 | 100/100 | 100/100 | 33/13 | 35/25 | 30/25 |
| 4D + 1 | 1.12 + 0.14 | 58/65 | 100/100 | 100/100 | 30/13 | 20/25 | 30/25 |
| 4D + 1 | 1.12 + 0.28 | 50/65 | 100/100 | 100/100 | 25/13 | 18/25 | 18/25 |
| 4D + 1 | 1.12 + 0.56 | 68/65 | 100/100 | 100/100 | 18/13 | 15/25 | 25/25 |
| 4D + 22 | 0.84 + 0.14 | 48/58 | 100/100 | 100/100 | 25/75 | 28/80 | 78/78 |
| 4D + 22 | 0.84 + 0.28 | 60/58 | 100/100 | 100/100 | 10/75 | 8/80 | 23/78 |
| 4D + 22 | 0.84 + 0.56 | 58/58 | 100/100 | 100/100 | 5/75 | 8/80 | 23/78 |
| 4D + 22 | 0.84 + 1.12 | 58/58 | 100/100 | 100/100 | 18/75 | 8/80 | 18/78 |
| 4D + 13 | 0.84 + 0.14 | 30/58 | 100/100 | 100/100 | 23/75 | 30/80 | 30/78 |
| 4D + 13 | 0.84 + 0.28 | 93/58 | 100/100 | 100/100 | 43/75 | 50/80 | 60/78 |
| 4D + 13 | 0.84 + 0.56 | 50/58 | 100/100 | 100/100 | 15/75 | 35/80 | 43/78 |
| 4D + 13 | 0.84 + 1.12 | 58/58 | 100/100 | 100/100 | 40/75 | 40/80 | 50/78 |
| 4D + 32 | 0.84 + 0.14 | 58/58 | 100/100 | 100/100 | 38/75 | 43/80 | 38/78 |
| 4D + 32 | 0.84 + 0.28 | 25/58 | 100/100 | 100/100 | 75/75 | 63/80 | 73/78 |
| 4D + 32 | 0.84 + 0.56 | 80/58 | 100/100 | 100/100 | 30/75 | 30/80 | 35/78 |
| 4D + 32 | 0.84 + 1.12 | 75/58 | 100/100 | 100/100 | 13/75 | 30/80 | 43/78 |
| RATING 20 DAYS AFTER TREATMENT | | | | | | | |
| 70D + 2 | 0.375 + 0.063 | 75/47 | 100/95 | 100/100 | 50/44 | 60/49 | 50/74 |
| 70D + 2 | 0.375 + 0.125 | 55/47 | 100/95 | 100/100 | 68/44 | 68/49 | 99/74 |
| 70D + 2 | 0.375 + 0.25 | 85/47 | 100/95 | 100/100 | 33/44 | 40/49 | 40/74 |
| 70D + 7 | 0.375 + 0.063 | 45/47 | 88/95 | 100/100 | 58/44 | 35/49 | 43/74 |

TABLE V-continued

| Treatment | Rate kg/ha Herb + Ant. | AMARE | SETVI | ECHCG | CN 64 | CN23A | CN3475 |
|---|---|---|---|---|---|---|---|
| 70D + 7 | 0.375 + 0.125 | 43/47 | 98/95 | 100/100 | 70/44 | 75/49 | 70/74 |
| 70D + 7 | 0.375 + 0.25 | 38/47 | 100/95 | 100/100 | 65/44 | 58/49 | 85/74 |
| 70D + 9 | 0.375 + 0.063 | 38/47 | 75/95 | 100/100 | 25/44 | 40/49 | 43/74 |
| 70D + 9 | 0.375 + 0.125 | 88/47 | 88/95 | 100/100 | 68/44 | 73/49 | 88/74 |
| 70D + 9 | 0.375 + 0.25 | 35/47 | 100/95 | 100/100 | 60/44 | 65/49 | 70/74 |
| 70D + 18 | 0.375 + 0.063 | 30/47 | 83/95 | 98/100 | 25/44 | 45/49 | 45/49 |
| 70D + 18 | 0.375 + 0.125 | 63/47 | 95/95 | 100/100 | 45/44 | 65/49 | 70/49 |
| 70D + 18 | 0.375 + 0.25 | 63/47 | 85/95 | 100/100 | 50/44 | 73/49 | 85/49 |
| 70D + 25 | 0.375 + 0.063 | 43/47 | 88/95 | 100/100 | 38/44 | 45/49 | 68/49 |
| 70D + 25 | 0.375 + 0.125 | 45/47 | 95/95 | 100/100 | 45/44 | 80/49 | 90/49 |
| 70D + 25 | 0.375 + 0.25 | 83/47 | 95/95 | 100/100 | 63/44 | 60/49 | 75/49 |
| 70D + 29 | 0.375 + 0.063 | 25/47 | 100/100 | 100/100 | 60/44 | 60/49 | 73/49 |
| 70D + 29 | 0.375 + 0.125 | 38/47 | 98/100 | 100/100 | 58/44 | 65/44 | 83/49 |
| 70D + 29 | 0.375 + 0.25 | 33/47 | 88/100 | 100/100 | 58/44 | 73/44 | 93/49 |
| 8D + 2 | 0.75 + 0.063 | 99/97 | 100/100 | 100/100 | 20/23 | 23/28 | 22/41 |
| 8D + 2 | 0.75 + 0.125 | 95/97 | 100/100 | 100/100 | 20/23 | 20/28 | 20/41 |
| 8D + 2 | 0.75 + 0.25 | 68/97 | 100/100 | 100/100 | 13/23 | 15/28 | 23/41 |
| 8D + 7 | 0.75 + 0.063 | 83/97 | 98/100 | 100/100 | 28/23 | 30/28 | 25/41 |
| 8D + 7 | 0.75 + 0.125 | 100/97 | 100/100 | 100/100 | 20/23 | 20/28 | 18/41 |
| 8D + 7 | 0.75 + 0.25 | 88/97 | 100/100 | 100/100 | 15/23 | 10/28 | 15/41 |
| 8D + 9 | 0.75 + 0.063 | 95/97 | 95/100 | 100/100 | 3/23 | 5/28 | 25/41 |
| 8D + 9 | 0.75 + 0.125 | 85/97 | 100/100 | 100/100 | 13/23 | 18/28 | 23/41 |
| 8D + 9 | 0.75 + 0.25 | 88/97 | 100/100 | 100/100 | 5/23 | 10/28 | 13/41 |
| 8D + 18 | 0.75 + 0.063 | 100/97 | 95/100 | 100/100 | 8/23 | 10/28 | 33/41 |
| 8D + 18 | 0.75 + 0.125 | 98/97 | 100/100 | 100/100 | 18/23 | 45/28 | 43/41 |
| 8D + 18 | 0.75 + 0.25 | 88/97 | 100/100 | 100/100 | 28/23 | 25/28 | 38/41 |
| 8D + 25 | 0.75 + 0.063 | 80/97 | 100/100 | 100/100 | 15/23 | 23/28 | 28/41 |
| 8D + 25 | 0.75 + 0.125 | 95/97 | 100/100 | 100/100 | 33/23 | 38/28 | 50/41 |
| 8D + 25 | 0.75 + 0.25 | 98/97 | 100/100 | 100/100 | 58/23 | 35/28 | 55/41 |
| 8D + 29 | 0.75 + 0.063 | 88/97 | 100/100 | 100/100 | 5/23 | 3/28 | 13/41 |
| 8D + 29 | 0.75 + 0.125 | 88/97 | 85/100 | 100/100 | 13/23 | 13/23 | 20/41 |
| 8D + 29 | 0.75 + 0.25 | 100/97 | 100/100 | 100/100 | 8/23 | 10/23 | 13/41 |

TABLE V-A

| Treatment | Rate lb/A Herb + Ant. | AMARE | SETVI | ECHCG | CN 64 | CN23A | CN3475 |
|---|---|---|---|---|---|---|---|
| | RATING 23 DAYS AFTER TREATMENT | | | | | | |
| 24D + 19 | 0.75 + 0.063 | 35/53 | 95/98 | 95/100 | 5/13 | 5/15 | 15/18 |
| 24D + 19 | 0.75 + 0.125 | 75/53 | 100/98 | 100/100 | 40/13 | 50/15 | 60/18 |
| 24D + 19 | 0.75 + 0.25 | 100/53 | 100/98 | 100/100 | 20/13 | 35/15 | 40/18 |

TABLE V-A-continued

| Treatment | Rate lb/A Herb + Ant. | AMARE | SETVI | ECHCG | CN 64 | CN23A | CN3475 |
|---|---|---|---|---|---|---|---|
| 24D + 24 | 0.75 + 0.063 | 80/53 | 100/98 | 98/100 | 10/13 | 10/15 | 15/18 |
| 24D + 24 | 0.75 + 0.125 | 75/53 | 100/98 | 100/100 | 40/13 | 45/15 | 40/18 |
| 24D + 24 | 0.75 + 0.25 | 75/53 | 100/98 | 100/100 | 20/13 | 15/15 | 35/18 |
| 24D + 24 | 0.75 + 0.5 | 75/53 | 100/98 | 100/100 | 25/13 | 25/15 | 30/18 |
| 24D + 11 | 0.75 + 0.063 | 80/53 | 100/98 | 100/100 | 5/13 | 5/15 | 5/18 |
| 24D + 11 | 0.75 + 0.125 | 95/53 | 100/98 | 100/100 | 35/13 | 40/15 | 35/18 |
| 24D + 11 | 0.75 + 0.25 | 100/53 | 100/98 | 100/100 | 10/13 | 15/15 | 20/18 |
| 24D + 11 | 0.75 + 0.5 | 100/53 | 100/98 | 100/100 | 20/13 | 25/15 | 20/18 |
| 24D + 12 | 0.75 + 0.063 | 85/53 | 100/98 | 100/100 | 5/13 | 0/15 | 5/18 |
| 24D + 12 | 0.75 + 0.125 | 60/53 | 100/98 | 100/100 | 35/13 | 25/15 | 25/18 |
| 24D + 12 | 0.75 + 0.25 | 98/53 | 100/98 | 100/100 | 10/13 | 25/15 | 30/18 |
| 24D + 12 | 0.75 + 0.5 | 98/53 | 100/98 | 100/100 | 10/13 | 25/15 | 20/18 |
| 24D + 14 | 0.75 + 0.063 | 75/53 | 100/98 | 100/100 | 0/13 | 0/15 | 0/18 |
| 24D + 14 | 0.75 + 0.125 | 100/53 | 100/98 | 100/100 | 35/13 | 25/15 | 25/18 |
| 24D + 14 | 0.75 + 0.25 | 100/53 | 100/98 | 100/100 | 5/13 | 15/15 | 20/18 |
| 24D + 14 | 0.75 + 0.5 | 100/53 | 100/98 | 100/100 | 5/13 | 35/15 | 25/18 |
| 24D + 16 | 0.75 + 0.063 | 75/53 | 100/98 | 100/100 | 10/13 | 10/15 | 10/18 |
| 24D + 16 | 0.75 + 0.125 | 90/53 | 100/98 | 100/100 | 5/13 | 15/15 | 25/18 |
| 24D + 16 | 0.75 + 0.25 | 100/53 | 100/98 | 100/100 | 30/13 | 35/15 | 35/18 |
| 24D + 16 | 0.75 + 0.5 | 70/53 | 100/98 | 100/100 | 35/13 | 40/15 | 45/18 |
| 24D + 17 | 0.75 + 0.063 | 100/53 | 100/98 | 100/100 | 5/13 | 0/15 | 10/18 |
| 24D + 17 | 0.75 + 0.125 | 100/53 | 100/98 | 100/100 | 5/13 | 10/15 | 10/18 |
| 24D + 17 | 0.75 + 0.25 | 100/53 | 100/98 | 100/100 | 60/13 | 60/15 | 60/18 |
| 24D + 17 | 0.75 + 0.5 | 100/53 | 100/98 | 100/100 | 20/13 | 30/15 | 35/18 |
| 24D + 20 | 0.75 + 0.063 | 100/53 | 100/98 | 100/100 | 15/13 | 25/15 | 5/18 |
| 24D + 20 | 0.75 + 0.125 | 90/53 | 100/98 | 100/100 | 30/13 | 50/15 | 40/18 |
| 24D + 20 | 0.75 + 0.25 | 90/53 | 100/98 | 100/100 | 30/13 | 40/15 | 40/18 |
| 24D + 20 | 0.75 + 0.5 | 100/53 | 100/98 | 100/100 | 35/13 | 40/15 | 30/18 |
| 24D + 23 | 0.75 + 0.063 | 75/53 | 100/98 | 100/100 | 5/13 | 10/15 | 5/18 |
| 24D + 23 | 0.75 + 0.125 | 95/53 | 100/98 | 100/100 | 40/13 | 50/15 | 40/18 |
| 24D + 23 | 0.75 + 0.25 | 100/53 | 100/98 | 100/100 | 5/13 | 15/15 | 20/18 |
| 24D + 23 | 0.75 + 0.5 | 90/53 | 100/98 | 100/100 | 5/13 | 0/15 | 25/18 |
| RATING 24 DAYS AFTER TREATMENT | | | | | | | |
| 4D + 8 | 0.75 + 0.125 | 25/100 | 100/100 | 100/100 | 5/40 | 10/35 | 5/35 |
| 4D + 8 | 0.75 + 0.25 | 100/100 | 100/100 | 100/100 | 5/40 | 5/35 | 35/35 |
| 4D + 8 | 0.75 + 0.5 | 100/100 | 100/100 | 100/100 | 10/40 | 5/35 | 20/35 |
| 4D + 8 | 0.75 + 1.0 | 100/100 | 100/100 | 100/100 | 10/40 | 10/35 | 10/35 |
| 4D + 10 | 0.75 + 0.125 | 90/100 | 100/100 | 100/100 | 5/40 | 5/35 | 20/35 |
| 4D + 10 | 0.75 + 0.25 | 95/100 | 100/100 | 100/100 | 5/40 | 10/35 | 15/35 |
| 4D + 10 | 0.75 + 0.5 | 95/100 | 100/100 | 100/100 | 15/40 | 20/35 | 40/35 |

TABLE V-A-continued

| Treatment | Rate lb/A Herb + Ant. | AMARE | SETVI | ECHCG | CN 64 | CN23A | CN3475 |
|---|---|---|---|---|---|---|---|
| 4D + 10 | 0.75 + 1.0 | 98/100 | 100/100 | 100/100 | 15/40 | 15/35 | 40/35 |
| 4D + 30 | 0.75 + 0.125 | 98/100 | 100/100 | 100/100 | 5/40 | 10/35 | 5/35 |
| 4D + 30 | 0.75 + 0.25 | 100/100 | 100/100 | 100/100 | 20/40 | 30/35 | 40/35 |
| 4D + 30 | 0.75 + 0.5 | 100/100 | 100/100 | 100/100 | 10/40 | 10/35 | 35/35 |
| 4D + 30 | 0.75 + 1.0 | 100/100 | 100/100 | 100/100 | 15/40 | 30/35 | 45/35 |
| 4D + 31 | 0.75 + 0.125 | 100/100 | 100/100 | 100/100 | 10/40 | 10/35 | 10/35 |
| 4D + 31 | 0.75 + 0.25 | 100/100 | 100/100 | 100/100 | 15/40 | 40/35 | 40/35 |
| 4D + 31 | 0.75 + 0.5 | 100/100 | 100/100 | 100/100 | 60/40 | 60/35 | 60/35 |
| 4D + 31 | 0.75 + 1.0 | 100/100 | 100/100 | 100/100 | 35/40 | 30/35 | 40/35 |
| 4D + 15 | 0.75 + 0.125 | 75/100 | 95/100 | 95/100 | 5/40 | 0/35 | 10/35 |
| 4D + 15 | 0.75 + 0.25 | 100/100 | 100/100 | 100/100 | 10/40 | 10/35 | 15/35 |
| 4D + 15 | 0 75 + 0.5 | 100/100 | 100/100 | 100/100 | 10/40 | 10/35 | 10/35 |
| 4D + 15 | 0.75 + 1.0 | 100/100 | 100/100 | 100/100 | 5/40 | 10/35 | 20/35 |
| RATING 25 DAYS AFTER TREATMENT ||||||||
| 4D + 25 | 0.75 + 0.063 | 100/70 | 100/95 | 99/100 | 8/15 | 3/5 | 3/13 |
| 4D + 25 | 0.75 + 0.125 | 75/70 | 95/95 | 95/100 | 23/15 | 18/5 | 23/13 |
| 4D + 25 | 0.75 + 0.25 | 98/70 | 100/95 | 100/100 | 23/15 | 13/5 | 15/13 |
| 4D + 25 | 0.75 + 0.5 | 99/70 | 98/95 | 98/100 | 5/15 | 3/5 | 8/13 |
| 4D + 26 | 0.75 + 0.063 | 100/70 | 99/95 | 99/100 | 0/15 | 0/5 | 3/13 |
| 4D + 26 | 0.75 + 0.125 | 100/70 | 100/95 | 95/100 | 13/15 | 5/5 | 3/13 |
| 4D + 26 | 0.75 + 0.25 | 95/70 | 100/95 | 98/100 | 3/15 | 0/5 | 28/13 |
| 4D + 26 | 0.75 + 0.5 | 100/70 | 100/95 | 98/100 | 3/15 | 0/5 | 18/13 |
| 4D + 27 | 0.75 + 0.063 | 75/70 | 100/95 | 99/100 | 13/15 | 0/5 | 0/13 |
| 4D + 27 | 0.75 + 0.125 | 98/70 | 100/95 | 100/100 | 10/15 | 10/5 | 13/13 |
| 4D + 27 | 0.75 + 0.25 | 70/70 | 99/95 | 100/100 | 5/15 | 13/5 | 18/13 |
| 4D + 27 | 0.75 + 0.5 | 100/70 | 100/95 | 98/100 | 15/15 | 15/5 | 18/13 |
| 4D + 27 | 0.75 + 0.063 | 85/70 | 100/95 | 98/100 | 18/15 | 10/5 | 13/13 |
| 4D + 27 | 0.75 + 0.125 | 98/70 | 95/95 | 95/100 | 10/15 | 13/5 | 13/13 |
| 4D + 27 | 0.75 + 0.25 | 80/70 | 100/95 | 100/100 | 28/15 | 13/5 | 15/13 |
| 4D + 27 | 0.75 + 0.5 | 95/70 | 100/95 | 100/100 | 15/15 | 13/5 | 13/13 |
| 4D + 5 | 0.75 + 0.167 | 80/70 | 88/95 | 93/100 | 5/15 | 8/5 | 8/13 |
| 4D + 5 | 0.75 + 0.33 | 98/70 | 100/95 | 100/100 | 10/15 | 10/5 | 13/13 |
| 4D + 5 | 0.75 + 0.67 | 100/70 | 100/95 | 100/100 | 18/15 | 15/5 | 15/13 |

TABLE V-B

RATING 24 DAYS AFTER TREATMENT

| Treatment | Rate kg/ha Herb + Ant. | AMARE | SETVI | ECHCG | CN 64 | CN23A | C3475 |
|---|---|---|---|---|---|---|---|
| 24D + 21 | 0.28 + 0.14 | 85/95 | 100/100 | 100/100 | 60/75 | 65/83 | 95/100 |
| 24D + 21 | 0.28 + 0.28 | 100/95 | 100/100 | 100/100 | 45/75 | 55/83 | 83/100 |
| 24D + | 0.28 + | 98/95 | 100/100 | 100/100 | 70/75 | 80/83 | 95/100 |

TABLE V-B-continued

RATING 24 DAYS AFTER TREATMENT

| Treatment | Rate kg/ha Herb + Ant. | AMARE | SETVI | ECHCG | CN 64 | CN23A | C3475 |
|---|---|---|---|---|---|---|---|
| 21 | 0.56 | | | | | | |
| 24D + 21 | 0.56 + 0.14 | 100/95 | 100/100 | 100/100 | 95/95 | 100/99 | 100/100 |
| 24D + 21 | 0.56 + 0.28 | 83/95 | 100/100 | 100/100 | 68/95 | 88/99 | 93/100 |
| 24D + 21 | 0.56 + 0.56 | 100/95 | 100/100 | 100/100 | 93/95 | 100/99 | 100/100 |
| 4D + 21 | 0.56 + 0.14 | 50/73 | 100/100 | 100/100 | 8/15 | 10/15 | 35/23 |
| 4D + 21 | 0.56 + 0.28 | 73/73 | 100/100 | 100/100 | 18/15 | 10/15 | 20/23 |
| 4D + 21 | 0.56 + 0.56 | 38/73 | 100/100 | 100/100 | 18/15 | 10/15 | 18/23 |
| 4D + 21 | 0.84 + 0.14 | 73/95 | 100/100 | 100/100 | 20/30 | 23/33 | 45/45 |
| 4D + 21 | 0.84 + 0.28 | 63/95 | 100/100 | 100/100 | 20/30 | 18/33 | 30/45 |
| 4D + 21 | 0.84 + 0.56 | 68/95 | 100/100 | 100/100 | 20/30 | 15/33 | 25/45 |

TABLES VI, VII, VIII, IX, X, XI

The following compounds were employed as examples of antidotes in Tables VI, VII, VIII, IX, X and XI, as indicated in the respective tables.

18  2,2-dimethyl-3-dichloroacetyl-5-n-propyl oxazolidine
19  3-(dichloroacetyl)-2,2,5-trimethyl thiazolidine
33  2,2-dimethyl-N-dichloroacetyl-5-isopropoxymethyl oxazolidine
25  2,2-dimethyl-3-dichloroacetyl-5-methoxymethyl oxazolidine
26  2,2-dimethyl-3-dichloroacetyl-5-ethoxymethyl oxazolidine
29  2,2-dimethyl-3-dichloroacetyl-5-ethyl-thiomethyl oxazolidine
34  2-2-dimethyl-3-(dichloroacetyl)-5-(ethylsulfonylmethyl)-1,3,oxazolidine
35  2-methyl-2-carboethoxymethyl-3-dichloroacetyl thiazolidine
36  2-methyl-2-carbomethoxymethyl-3-dichloroacetyl thiazolidine
37  2-methyl-2-ethyl-3-dichloroacetyl-1,3-thiazolidine
38  2-butyn-1-yl-p-toluenesulfonyl carbamate
39  2,2,2-trifluoroethyl-p-chlorophenyl carbamate Procedures for Tables VI, VII, VIII and IX are substantially the same as given above. Crop seeds and weeds were as follows:

Weed:
SETVI—green foxtail (*Sertaria viridis*)
ECHCG—watergrass (*Echinochloa crusgalli*)
AMARE—redroot pigweed (*Amaranthus retroflexus*)
Crop: Corn Varieties CN64; CN72AA; XL55; CN23A; CN447; CN3475 CN405W; CN7780; CN3541; CN7751; CN22; CN5340; CN8415; CN Golden Jubilee (CN GJ) CN6060; CNC6595; CNL17; CNLH74; CNL123; CN179; CN872; CN59; CN73; CN397; CN4256; CN3535; CN1100.

TABLE VI

Rating 29 Days after Treatment

| Treatment | Rate lb/A Herb + Ant. | SETVI | CN64 | CN 72AA | XL55 | CN23A | CN447 | ECHOG | CN 3475 | CN 405W | CN 7780 | CN 3541 | CN 7751 |
|---|---|---|---|---|---|---|---|---|---|---|---|---|---|
| 4D + 2 | 0.75 + 0.063 | 100/100 | 3/20 | 5/25 | 3/23 | 3/18 | 23/38 | 100/100 | 0/10 | 0/10 | 0/18 | 15/38 | 5/58 |
| 4D + 2 | 0.75 + 0.125 | 100/100 | 3/20 | 18/25 | 8/23 | 10/18 | 3/38 | 100/100 | 5/10 | 13/10 | 3/18 | 48/38 | 8/58 |
| 4D + 2 | 0.75 + 0.25 | 100/100 | 5/20 | 10/25 | 3/23 | 4/18 | 8/38 | 100/100 | 0/10 | 0/10 | 0/18 | 68/38 | 3/58 |
| 4D + 6 | 0.75 + 0.063 | 100/100 | 5/20 | 10/25 | 3/23 | 4/18 | 5/38 | 100/100 | 10/10 | 3/10 | 8/18 | 15/38 | 13/58 |
| 4D + 6 | 0.75 + 0.125 | 100/100 | 8/20 | 20/25 | 5/23 | 5/18 | 5/38 | 100/100 | 5/10 | 10/10 | 5/18 | 70/38 | 18/58 |
| 4D + 6 | 0.75 + 0.25 | 100/100 | 10/20 | 18/25 | 13/23 | 8/18 | 8/38 | 100/100 | 5/10 | 3/10 | 5/18 | 0/38 | 10/58 |
| 4D + 6 | 0.75 + 0.5 | 100/100 | 10/20 | 23/25 | 0/23 | 5/18 | 5/38 | 100/100 | 8/10 | 5/10 | 8/18 | 0/38 | 10/58 |
| 4D + 7 | 0.75 + 0.063 | 100/100 | 10/20 | 25/25 | 10/23 | 8/18 | 15/38 | 100/100 | 3/10 | 5/10 | 3/18 | 50/38 | 3/58 |
| 4D + 7 | 0.75 + 0.125 | 100/100 | 3/20 | 8/25 | 0/23 | 5/18 | 8/38 | 100/100 | 0/10 | 0/10 | 0/18 | 0/38 | 4/58 |
| 4D + 7 | 0.75 + 0.25 | 100/100 | 5/20 | 13/25 | 5/23 | 0/18 | 3/38 | 100/100 | 0/10 | 5/10 | 5/18 | 50/38 | 0/58 |
| 4D + 7 | 0.75 + 0.5 | 100/100 | 5/20 | 0/25 | 0/23 | 0/18 | 5/38 | 100/100 | 0/10 | 0/10 | 5/18 | 0/38 | 0/58 |
| 4D + 18 | 0.75 + 0.063 | 100/100 | 8/20 | 5/25 | 3/23 | 3/18 | 8/38 | 100/100 | 0/10 | 0/10 | 0/18 | 0/38 | 5/58 |
| 4D + 18 | 0.75 + 0.125 | 100/100 | 8/20 | 10/25 | 8/23 | 5/18 | 8/38 | 100/100 | 3/10 | 8/10 | 18/18 | 50/38 | 10/58 |
| 4D + 18 | 0.75 + 0.25 | 100/100 | 8/20 | 23/25 | 15/23 | 3/18 | 3/38 | 100/100 | 5/10 | 5/10 | 5/18 | 80/38 | 5/58 |
| 4D + | 0.75 + | 100/100 | 13/20 | 5/25 | 0/23 | 5/18 | 18/38 | 100/100 | 3/10 | 3/10 | 8/18 | 13/38 | 18/58 |

TABLE VI-continued

Rating 29 Days after Treatment

| Treatment | Rate lb/A Herb + Ant. | SETVI | CN64 | CN 72AA | XL55 | CN23A | CN447 | ECHOG | CN 3475 | CN 405W | CN 7780 | CN 3541 | CN 7751 |
|---|---|---|---|---|---|---|---|---|---|---|---|---|---|
| 18 | 0.5 | | | | | | | | | | | | |
| 4D + 33 | 0.75 + 0.063 | 100/100 | 3/20 | 13/25 | 10/23 | 5/18 | 3/38 | 100/100 | 0/10 | 0/10 | 0/18 | 0/38 | 3/58 |
| 4D + 33 | 0.75 + 0.125 | 100/100 | 0/20 | 3/25 | 0/23 | 0/18 | 5/38 | 100/100 | 3/10 | 8/10 | 3/18 | 50/38 | 10/58 |
| 4D + 33 | 0.75 + 0.25 | 100/100 | 3/20 | 5/25 | 3/23 | 0/18 | 3/38 | 100/100 | 3/10 | 0/10 | 0/18 | 3/38 | 3/58 |
| 4D + 33 | 0.75 + 0.5 | 99/100 | 3/20 | 5/25 | 0/23 | 0/18 | 8/38 | 100/100 | 0/10 | 3/10 | 3/18 | 10/38 | 5/58 |
| 4D + 29 | 0.75 + 0.063 | 100/100 | 0/20 | 0/25 | 0/23 | 0/18 | 0/38 | 100/100 | 3/10 | 0/10 | 3/18 | 0/38 | 3/58 |
| 4D + 29 | 0.75 + 0.125 | 100/100 | 5/20 | 3/25 | 0/23 | 0/18 | 0/38 | 100/100 | 0/10 | 0/10 | 0/18 | 0/38 | 0/58 |
| 4D + 29 | 0.75 + 0.25 | 100/100 | 3/20 | 0/25 | 5/23 | 0/18 | 8/38 | 100/100 | 3/10 | 0/10 | 13/18 | 50/38 | 3/58 |
| 4D + 29 | 0.75 + 0.5 | 100/100 | 5/20 | 0/25 | 0/23 | 3/18 | 0/38 | 98/100 | 3/10 | 0/10 | 0/18 | 0/38 | 0/58 |
| 4D + 34 | 0.75 + 0.063 | 100/100 | 10/20 | 13/25 | 5/23 | 0/18 | 3/38 | 100/100 | 3/10 | 0/10 | 3/18 | 3/38 | 5/58 |
| 4D + 34 | 0.75 + 0.125 | 100/100 | 3/20 | 23/25 | 0/23 | 3/18 | 3/38 | 100/100 | 0/10 | 3/10 | 0/18 | 25/38 | 10/58 |
| 4D + 34 | 0.75 + 0.25 | 100/100 | 10/20 | 13/25 | 13/23 | 3/18 | 0/38 | 100/100 | 3/10 | 0/10 | 3/18 | 3/38 | 3/58 |
| 4D + 34 | 0.75 + 0.5 | 100/100 | 0/20 | 0/25 | 0/23 | 0/18 | 0/38 | 100/100 | 0/10 | 10/10 | 8/18 | 0/38 | 3/58 |

TABLE VII

Rating 27 Days After Treatment

| Treatment | Rate lb/A Herb + Ant. | SETVI | CN22 | CN 5340 | CN 8415 | CN GJ | ECHOG | CN 6060 | CN C596 | CN L117 | CN LH74 | CN L123 |
|---|---|---|---|---|---|---|---|---|---|---|---|---|
| 4D + 2 | 1.0 + 0.063 | 100/99 | 23/26 | 18/28 | 20/42 | 75/81 | 100/100 | 8/15 | 8/11 | 13/34 | 8/23 | 30/27 |
| 4D + 2 | 1.0 + 0.125 | 100/99 | 8/26 | 3/28 | 5/42 | 60/81 | 100/100 | 8/15 | 3/11 | 13/34 | 5/23 | 8/27 |
| 4D + 2 | 1.0 + 0.25 | 85/99 | 10/26 | 10/28 | 38/42 | 98/81 | 100/100 | 10/15 | 13/11 | 15/34 | 23/23 | 15/27 |
| 4D + 7 | 1.0 + 0.063 | 100/99 | 15/26 | 13/28 | 18/42 | 100/81 | 100/100 | 8/15 | 0/11 | 10/34 | 10/23 | 8/27 |
| 4D + 7 | 1.0 + 0.125 | 100/99 | 18/26 | 28/28 | 28/42 | 95/81 | 100/100 | 10/15 | 3/11 | 25/34 | 23/23 | 15/27 |
| 4D + 7 | 1.0 + 0.25 | 100/99 | 25/26 | 20/28 | 20/42 | 100/81 | 100/100 | 18/15 | 8/11 | 18/34 | 20/23 | 5/27 |
| 4D + 9 | 1.0 + 0.063 | 99/99 | 15/26 | 23/28 | 18/42 | 70/81 | 100/100 | 10/15 | 8/11 | 13/34 | 10/23 | 8/27 |
| 4D + 9 | 1.0 + 0.125 | 100/99 | 5/26 | 5/28 | 10/42 | 50/81 | 100/100 | 5/15 | 5/11 | 8/34 | 8/23 | 10/27 |
| 4D + 9 | 1.0 + 0.25 | 100/99 | 20/26 | 8/28 | 15/42 | 55/81 | 100/100 | 13/15 | 8/11 | 15/34 | 25/23 | 8/27 |
| 4D + 33 | 1.0 + 0.063 | 100/99 | 8/26 | 3/28 | 30/42 | 58/81 | 100/100 | 5/15 | 5/11 | 3/34 | 3/23 | 5/27 |
| 4D + 33 | 1.0 + 0.125 | 100/99 | 10/26 | 18/28 | 18/42 | 75/81 | 100/100 | 5/15 | 15/11 | 8/34 | 15/23 | 28/27 |
| 4D + 33 | 1.0 + 0.25 | 100/99 | 20/26 | 18/28 | 3/42 | 95/81 | 100/100 | 8/15 | 8/11 | 13/34 | 10/23 | 10/27 |
| 4D + 29 | 1.0 + 0.063 | 85/99 | 8/26 | 8/28 | 10/42 | 58/81 | 100/100 | 3/15 | 3/11 | 3/34 | 5/23 | 5/27 |
| 4D + 29 | 1.0 + 0.125 | 100/99 | 3/26 | 3/28 | 8/42 | 50/81 | 100/100 | 8/15 | 5/11 | 8/34 | 5/23 | 3/27 |
| 4D + 29 | 1.0 + 0.25 | 95/99 | 5/26 | 4/28 | 10/42 | 75/81 | 100/100 | 8/15 | 5/11 | 5/34 | 10/23 | 8/27 |
| 4D + 34 | 1.0 + 0.063 | 100/99 | 15/26 | 10/28 | 10/42 | 45/81 | 100/100 | 8/15 | 3/11 | 10/34 | 18/23 | 25/27 |
| 4D + 34 | 1.0 + 0.125 | 100/99 | 13/26 | 10/28 | 18/42 | 75/81 | 100/100 | 10/15 | 0/11 | 8/34 | 5/23 | 5/27 |
| 4D + 34 | 1.0 + 0.25 | 100/99 | 8/26 | 10/28 | 8/42 | 28/81 | 100/100 | 5/15 | 5/11 | 10/34 | 15/23 | 15/27 |
| 4D + 25 | 1.0 + 0.063 | 100/99 | 38/26 | 40/28 | 80/42 | 100/81 | 99/100 | 28/15 | 13/11 | 68/34 | 40/23 | 53/27 |
| 4D + 25 | 1.0 + 0.125 | 100/99 | 35/26 | 33/28 | 43/42 | 99/81 | 98/100 | 10/15 | 13/11 | 55/34 | 65/23 | 65/27 |
| 4D + 25 | 1.0 + 0.25 | 55/99 | 38/26 | 25/28 | 15/42 | 50/81 | 100/100 | 20/15 | 8/11 | 33/34 | 38/23 | 43/27 |
| 4D + 26 | 1.0 + 0.063 | 100/99 | 30/26 | 15/28 | 20/42 | 25/81 | 100/100 | 8/15 | 5/11 | 10/34 | 28/23 | 35/27 |

TABLE VII-continued

Rating 27 Days After Treatment

| Treatment | Rate lb/A Herb + Ant. | SETVI | CN22 | CN 5340 | CN 8415 | CN GJ | ECHOG | CN 6060 | CN C596 | CN L117 | CN LH74 | CN L123 |
|---|---|---|---|---|---|---|---|---|---|---|---|---|
| 4D + 26 | 1.0 + 0.125 | 100/99 | 15/26 | 13/28 | 23/42 | 90/81 | 100/100 | 13/15 | 3/11 | 3/34 | 10/23 | 30/27 |
| 4D + 26 | 1.0 + 0.25 | 100/99 | 8/26 | 20/28 | 13/42 | 88/81 | 100/100 | 13/15 | 13/11 | 5/34 | 0/23 | 20/27 |
| 4D + 18 | 1.0 + 0.063 | 100/99 | 33/26 | 43/28 | 25/42 | 45/81 | 100/100 | 20/15 | 15/11 | 18/34 | 15/23 | 38/27 |
| 4D + 18 | 1.0 + 0.125 | 100/99 | 35/26 | 35/28 | 38/42 | 80/81 | 100/100 | 8/15 | 10/11 | 10/34 | 10/23 | 35/27 |
| 4D + 18 | 1.0 + 0.25 | 100/99 | 28/26 | 35/28 | 43/42 | 100/81 | 100/100 | 13/15 | 5/11 | 28/34 | 5/23 | 25/27 |
| 4D + 19 | 1.0 + 0.063 | 95/99 | 8/26 | 23/28 | 38/42 | 88/81 | 100/100 | 8/15 | 3/11 | 28/34 | 5/23 | 33/27 |
| 4D + 19 | 1.0 + 0.125 | 100/99 | 30/26 | 33/28 | 40/42 | 100/81 | 100/100 | 33/15 | 18/11 | 53/34 | 40/23 | 40/27 |
| 4D + 19 | 1.0 + 0.25 | 100/99 | 50/26 | 38/28 | 43/42 | 95/81 | 100/100 | 30/15 | 15/11 | 23/34 | 15/23 | 53/27 |

TABLE VIII

Rating 26 Days After Treatment

| Treatment | Rate lb/A Herb/Ant. | SETVI | CN 7751 | CN179 | CN872 | CN59 | CN 8415 | CN73 | CN397 | CN 4256 | CN 3535 | CN 1100 |
|---|---|---|---|---|---|---|---|---|---|---|---|---|
| 4D + 37 | 1.0 + 0.063 | 100/100 | 25/35 | 0/30 | 0/0 | 0/5 | 10/35 | 0/25 | 0/10 | 0/100 | 0/10 | 0/20 |
| 4D + 37 | 1.0 + 0.125 | 100/100 | 20/35 | 50/30 | 0/0 | 50/5 | 35/35 | 40/25 | 35/10 | 10/100 | 10/10 | 5/20 |
| 4D + 37 | 1.0 + 0.25 | 100/100 | 15/35 | 25/30 | 5/0 | 40/5 | 20/35 | 15/25 | 0/10 | 40/100 | 10/10 | 20/20 |
| 4D + 37 | 1.0 + 0.5 | 100/100 | 10/35 | 10/30 | 0/0 | 40/5 | 20/35 | 50/25 | 15/10 | 15/100 | 15/10 | 10/20 |
| 4D + 37 | 1.75 + 0.063 | 100/100 | 10/60 | 10/70 | 0/45 | 75/70 | 40/100 | 40/95 | 0/35 | 20/50 | 20/25 | 10/15 |
| 4D + 37 | 1.75 + 0.5 | 100/100 | 25/60 | 65/70 | 30/45 | 70/70 | 40/100 | 60/95 | 30/35 | 10/50 | 10/25 | 15/15 |

TABLE IX

Rating 13 Days after Treatment

| Treatment | Rate lb/A Herb + Ant. | AMARE | SETVI | CN7751 | CN8415 | CN73 | CN179 |
|---|---|---|---|---|---|---|---|
| 4D + 35 | 1.0 + 0.063 | 73/78 | 100/100 | 65/88 | 43/83 | 50/90 | 50/90 |
| 4D + 35 | 1.0 + 0.125 | 100/78 | 98/100 | 55/88 | 75/83 | 80/90 | 80/90 |
| 4D + 35 | 1.0 + 0.25 | 88/78 | 100/100 | 65/88 | 68/83 | 75/90 | 78/90 |
| 4D + 36 | 1.0 + 0.5 | 93/78 | 100/100 | 58/88 | 58/83 | 75/90 | 80/90 |
| 4D + 36 | 1.0 + 0.063 | 88/78 | 100/100 | 85/88 | 75/83 | 88/90 | 85/90 |
| 4D + 36 | 1.0 + 0.125 | 98/78 | 100/100 | 58/88 | 63/83 | 85/90 | 85/90 |
| 4D + 36 | 1.0 + 0.25 | 95/78 | 100/100 | 68/88 | 40/83 | 68/90 | 68/90 |
| 4D + 36 | 1.0 + 0.5 | 93/78 | 100/100 | 43/88 | 53/83 | 73/90 | 75/90 |

Compound IV-13 (original sample) was applied as a pre-emergence tank-mix with either Compound 1, Compound 2, Compound 9, Compound 13 or Compound 39. The herbicide and/or antidote were applied on three corn hybrids: (Zea mays), barley, milo, wheat, rice and on the weeds ELEIN and ABUTH. All compounds were technical and dissolved in a 60:40 acetone/water rati with 0.5% Tween 20° added. All seeds were planted 2 cm deep i aluminum flats (10×21×6 cm deep); soil type was a sandy loam soil, pH 6.7, containing 0.8% O.M. and 8.95 clay. Soil was fortified with fertilizer (17-17-17) and Captan 80W ® prior to seeding. Applications were made with the carrier volume of 25 gal/A. Ratings were conducted 18 days after treatment.

TABLE X

| Compound | Herbicide + Antidote Rate (lb/A) | ML | RC201 | ELEIN | ABUTH |
|---|---|---|---|---|---|

TABLE X-continued

| Compound | Rate (lb/A) | | | | |
|---|---|---|---|---|---|
| IV-13 + 1 | 0.625 + 0.50 | 25/40 | 10/15 | 20/15 | 0/15 |
| | 0.625 + 1.00 | 25/40 | 0/15 | 50/15 | 50/15 |
| | 0.625 + 2.00 | 15/40 | 0/15 | 40/15 | 15/15 |
| | 0.125 + 0.50 | 50/65 | 5/15 | 20/20 | 0/20 |
| | 0.125 + 1.00 | 70/65 | 10/15 | 50/20 | 35/20 |
| | 0.125 + 2.00 | 35/65 | 0/15 | 30/20 | 20/20 |
| IV-13 + 2 | 0.625 + 0.25 | 15/40 | 0/15 | 20/15 | 10/15 |
| | 0.625 + 0.50 | 20/40 | 0/15 | 20/15 | 15/15 |
| | 0.625 + 1.00 | 20/40 | 0/15 | 35/15 | 10/15 |
| | 0.125 + 0.25 | 40/65 | 25/15 | 40/20 | 50/20 |
| | 0.125 + 0.50 | 65/65 | 20/15 | 25/20 | 0/20 |
| | 0.125 + 1.00 | 40/65 | 30/15 | 50/20 | 40/20 |
| IV-13 + 13 | 0.625 + 0.50 | 35/40 | 0/15 | 40/15 | 0/15 |
| | 0.625 + 1.00 | 35/40 | 5/15 | 20/15 | 5/15 |
| | 0.625 + 2.00 | 30/40 | 0/15 | 65/15 | 0/15 |
| | 0.125 + 0.50 | 80/65 | 20/15 | 60/20 | 10/20 |
| | 0.125 + 1.00 | 60/65 | 15/15 | 50/20 | 15/20 |
| | 0.125 + 2.00 | 65/65 | 25/15 | 40/20 | 0/20 |
| IV-13 + 9 | 0.625 + 0.25 | 10/40 | 0/15 | 10/15 | 30/15 |
| | 0.625 + 0.50 | 15/40 | 0/15 | 25/15 | 0/15 |
| | 0.625 + 1.00 | 10/40 | 0/15 | 5/15 | 0/15 |
| | 0.125 + 0.25 | 20/65 | 15/15 | 65/20 | 10/20 |
| | 0.125 + 0.50 | 60/65 | 20/15 | 20/20 | 25/20 |
| | 0.125 + 1.00 | 40/65 | 30/15 | 30/20 | 0/20 |
| IV-13 + 39 | 0.625 + 0.50 | 25/40 | 0/15 | 20/15 | 15/15 |
| | 0.625 + 1.00 | 20/40 | 0/15 | 25/15 | 0/15 |
| | 0.625 + 2.00 | 20/40 | 0/15 | 20/15 | 20/15 |
| | 0.125 + 0.50 | 50/65 | 15/15 | 30/20 | 40/20 |
| | 0.125 + 1.00 | 60/65 | 10/15 | 30/20 | 30/20 |
| | 0.125 + 2.00 | 60/65 | 20/15 | 20/20 | 0/20 |

| Compound | Herbicide + Antidote Rate (lb/A) | ELEIN | ABUTH | CORN AVERAGE | BARLEY | WHEAT |
|---|---|---|---|---|---|---|
| IV-13 + 1 | 0.50 + 0.50 | 95/88 | 100/95 | 0/0 | 0/0 | 10/5 |
| | 0.50 + 1.00 | 90/88 | 100/95 | 0/0 | 0/0 | 25/5 |
| | 0.50 + 2.00 | 80/88 | 90/95 | 0/0 | 0/0 | 5/5 |
| | 1.00 + 0.50 | 100/98 | 100/93 | 0/0 | 0/0 | 10/10 |
| | 1.00 + 1.00 | 100/98 | 100/93 | 0/0 | 0/0 | 5/10 |
| | 1.00 + 2.00 | 85/98 | 85/93 | 0/0 | 0/0 | 5/10 |
| IV-13 + 2 | 0.50 + 0.25 | 85/88 | 95/95 | 0/0 | 0/0 | 0/5 |
| | 0.50 + 0.50 | 98/88 | 100/95 | 0/0 | 0/0 | 10/5 |
| | 0.50 + 1.00 | 98/88 | 100/95 | 0/0 | 0/0 | 15/5 |
| | 1.00 + 0.25 | 98/98 | 100/93 | 0/0 | 0/0 | 5/10 |
| | 1.00 + 0.50 | 80/98 | 100/93 | 0/0 | 0/0 | 5/10 |
| | 1.00 + 1.00 | 98/98 | 100/93 | 0/0 | 0/0 | 10/10 |
| IV-13 + 13 | 0.50 + 0.50 | 95/88 | 100/95 | 0/0 | 0/0 | 10/5 |
| | 0.50 + 1.00 | 90/88 | 100/95 | 0/0 | 0/0 | 15/5 |
| | 0.50 + 2.00 | 90/88 | 100/95 | 0/0 | 0/0 | 20/5 |
| | 1.00 + 0.50 | 75/98 | 100/93 | 0/0 | 0/0 | 10/10 |
| | 1.00 + 1.00 | 90/98 | 100/93 | 0/0 | 0/0 | 15/10 |
| | 1.00 + 2.00 | 70/98 | 90/93 | 0/0 | 0/0 | 10/10 |
| IV-13 + 9 | 0.50 + 0.25 | 85/88 | 100/95 | 0/0 | 0/0 | 10/5 |
| | 0.50 + 0.50 | 90/88 | 100/95 | 0/0 | 0/0 | 10/5 |
| | 0.50 + 1.00 | 95/88 | 100/95 | 0/0 | 0/0 | 5/5 |
| | 1.00 + 0.25 | 85/98 | 100/93 | 0/0 | 0/0 | 5/10 |
| | 1.00 + 0.50 | 90/98 | 100/93 | 0/0 | 0/0 | 15/10 |
| | 1.00 + 1.00 | 95/98 | 100/93 | 0/0 | 0/0 | 5/10 |
| IV-13 + 39 | 0.50 + 0.50 | 95/88 | 100/95 | 0/0 | 0/0 | 0/5 |
| | 0.50 + 1.00 | 85/88 | 100/95 | 0/0 | 0/0 | 10/5 |
| | 0.50 + 2.00 | 75/88 | 100/95 | 0/0 | 0/0 | 20/5 |
| | 1.00 + 0.50 | 100/98 | 100/93 | 0/0 | 0/0 | 25/10 |
| | 1.00 + 1.00 | 90/98 | 100/93 | 0/0 | 0/0 | 5/10 |
| | 1.00 + 2.00 | 85/98 | 100/93 | 0/0 | 0/0 | 10/10 |

TABLE XI

| Compound | Herbicide + Antidote Rate (lb/A) | SETVI | Average Corn* BL* | ST |
|---|---|---|---|---|
| Early Rating | | | | |
| 71D + 2 | 0.125 + 0.125 | 100/100 | 60/58 | 15/26 |
| | 0.125 + 0.250 | 100/100 | 39/58 | 13/26 |
| | 0.125 + 0.500 | 100/100 | 16/58 | 11/26 |
| | 0.250 + 0.125 | 100/100 | 68/41 | 29/14 |
| | 0.250 + 0.250 | 100/100 | 65/41 | 33/14 |
| | 0.250 + 0.500 | 100/100 | 63/41 | 31/14 |
| 71D + 9 | 0.125 + 0.125 | 100/100 | 0/58 | 0/26 |
| | 0.125 + 0.250 | 100/100 | 40/58 | 20/26 |
| | 0.125 + 0.500 | 100/100 | 15/58 | 10/26 |
| | 0.250 + 0.125 | 100/100 | 35/41 | 16/14 |
| | 0.250 + 0.250 | 100/100 | 53/41 | 19/14 |
| | 0.250 + 0.500 | 100/100 | 64/41 | 30/14 |
| 71D + 29 | 0.125 + 0.125 | 95/100 | 11/58 | 9/26 |
| | 0.125 + 0.250 | 100/100 | 39/58 | 19/26 |
| | 0.125 + 0.500 | 95/100 | 6/58 | 5/26 |
| | 0.250 + 0.125 | 100/100 | 35/41 | 16/14 |
| | 0.250 + 0.250 | 100/100 | 40/41 | 26/14 |
| | 0.250 + 0.500 | 100/100 | 45/41 | 33/14 |
| Late Rating | | | | |
| 71D + 2 | 0.125 + 0.125 | 100/100 | 15/3 | 25/49 |
| | 0.125 + 0.250 | 100/100 | 19/3 | 23/49 |
| | 0.125 + 0.500 | 100/100 | 9/3 | 21/49 |
| | 0.250 + 0.125 | 100/100 | 4/8 | 55/9 |

TABLE XI-continued

| Compound | Herbicide + Antidote Rate (lb/A) | SETVI | Average Corn* BL* | ST |
|---|---|---|---|---|
| | 0.250 + 0.250 | 100/100 | 9/8 | 30/9 |
| | 0.250 + 0.500 | 100/100 | 0/8 | 45/9 |
| 71D + 9 | 0.125 + 0.125 | 100/100 | 0/3 | 0/49 |
| | 0.125 + 0.250 | 100/100 | 1/3 | 0/49 |
| | 0.125 + 0.500 | 100/100 | 10/3 | 16/49 |
| 71D + 9 | 0.250 + 0.125 | 100/100 | 11/8 | 23/9 |
| | 0.250 + 0.250 | 100/100 | 9/8 | 16/9 |
| | 0.250 + 0.500 | 100/100 | 4/8 | 44/9 |
| 71D + 29 | 0.125 + 0.125 | 90/100 | 3/3 | 11/49 |
| | 0.125 + 0.250 | 100/100 | 0/3 | 0/49 |
| | 0.125 + 0.500 | 95/100 | 0/3 | 10/49 |
| 71d + 29 | 0.250 + 0.125 | 95/100 | 9/8 | 16/9 |
| | 0.250 + 0.250 | 100/100 | 6/8 | 23/9 |
| | 0.250 + 0.500 | 100/100 | 14/8 | 35/9 |

BL = Bleaching
ST = Stunting

TABLE XII
Seed Treatment

Herbicides: 8D and 51A
Antidote: Compound 32
Antidote was applied as a seed treatment
(0.0625% to 0.5% of the antidote by weight of the seed)
Planting was 2 cm deep in sandy loam soil.
Ratings were conducted 12 days after treatment and 21 days after treatment.
Two weed species: ABUTH velvetleaf (*Abutilon theophrasti*)
ELEIN goodgrass (*Eleusine indica*)
Corn varieties: Corn 3737
Corn 7751
Average represents average valued for bleaching (BL) and stunting (ST).

| Herbicide-Antidote Compounds | Time (days) | Rate (lb/A + w/w %) | ELEIN | ABUTH | Average Corn BL | ST |
|---|---|---|---|---|---|---|
| 8D 32 | 12 | 0.5 + 0.5% | 100/100 | 100/100 | 0/40 | 10/20 |
| | 21 | 0.5 + 0.5% | 100/100 | 100/100 | 0/20 | 10/33 |
| | | | | | CN 7751 | |
| 51A 32 | 20 | 1.0 + 0.5% | 100/100 | 100/100 | 0/18 | |

FORMULATIONS

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus of a crop where it is desired to establish herbicidal selectivity by a convenient method. The "locus" may include soil, seeds, crop, crop seeds, seedlings and vegetation.

The antidotes described herein can be formulated in a number of ways for suitable application: (a) the antidote can be formulated for application directly to the crop seed; (b) the antidote and herbicide may be formulated separately and applied separately or applied simultaneously in an appropriate weight ratio, e.g., as a tank mix, or (c) the antidote and herbicide may be formulated together in the proper weight ratio.

Useful formulations of the compounds of this invention can be prepared in conventional ways. They include dusts, granules, microcapsules, pellets, solutions, suspensions, emulsions, wettable powders, emulsifiable concentrates and the like. Many of these may be applied directly to the locus. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active herbicide and antidote ingredient(s) and at least one of (a) about 0.1% to 20% surfactant(s) and (b) about 1% to 99.9% solid or liquid inert diluent(s). More specifically, they can contain these ingredients in the following approximate proportions.

TABLE 2

| | Active Herb & Ant. Ingredients | Weight Percent* Diluent(s) | Surfactant(s) |
|---|---|---|---|
| Wettable Powders | 20–90 | 0–74 | 1–10 |
| Oil Suspensions Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formula or by tank mixing.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom sprayers, hand sprayers or airplanes.

Wettable powders are finely divided compositions comprising a particular carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Mercel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite sawdust, and granular carbon.

Microcapsules and other slow release formulations are advantageous as formulations to deliver and distribute the active ingredients. Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 90% of the weight of the entire capsule, and may contain an amount of solvent in addition to the active materials. Encapsulated granules are characterized by porous membranes sealing the openings of the granule carrier press, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention as well as materials in their naturally occurring form. Examples of such carriers are vermiculite, sintered clay granules, kaolin, attapulgite clay, sawdust and granular carbon. Useful encapsulating materials include natural and synthetic rubbers, cellulosic materials, styrene-butadiene copolymers, polyacrylonitriles, polyacrylates, polyesters, polyamides, polyureas, polyurethanes and starch xanthates.

Emulsifiable concentrates consist of an oil solution of the formulant plus an emulsifying agent. Prior to use, the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain seveal additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers or airplanes.

EXAMPLE

Dusts: The following substances are used to formulate (a) 5% and (b) a 2% dust:

(a)

5 parts of active substance
95 parts of talc;

(b)

2 parts of active substance
1 part of highly dispersed silicic acid
97 parts of talc.

The active substances are mixed with the carriers and ground and in this form can be processed to dusts for application.

EXAMPLE

Granulate: The following substances are used to formulate a 5% granulate:
5 parts of active substance
0.25 part of epichlorohydrin
0.25 part of cetyl polyglycol ether
3.25 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

EXAMPLE

Wettable powders: The following constituents are used to formula (a) a 70%, (b) a 40%, (c) and (d) a 25% and (e) a 10% wettable powder.

(a)

70 parts of active substance
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk (b)

40 parts of active substance
5 parts of sodium ligninsulfonate
1 part of sodium dibutylnaphthalenesulfonic acid
54 parts of silicic acid (c)

25 parts of active substance
4.5 parts of calcium ligninsulfate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk 28.1 parts of kaolin (d)

25 parts of active substance
2.5 parts of isoctylphenoxy-polyethylene-ethanol
1.7 parts of a Champagne chalk/hydroxyethyl cellulose mixture (1:1)
8.3 parts of sodium aluminum silicate
16.5 parts of kieselguhr
46 parts of kaolin (e)

10 parts of active substance
3 parts of a mixture of the sodium salts of saturated fatty alcohol sulfates
5 parts of naphthalenesulfonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants.

EXAMPLE

Emulsifiable concentrate: The following substances are used to formulate a 25% emulsifiable concentrate:
25 parts of active substance
2.5 parts of epoxidized vegetable oil
10 parts of an alkylarylsulfonate/fatty alcohol polyglycol ether mixture
5 parts of dimethylformamide
57.5 parts of xylene.

By diluting such a concentrate with water it is possible to prepare emulsions of the desired concentrations, which are especially suitable for leaf application.

What is claimed is:

1. A herbicide composition wherein said herbicidally active ingredient is a compound of the formula

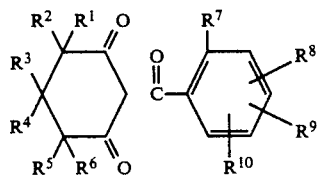

in which
R$^1$, R$^2$, R$^3$, R$^4$, R$^5$ and R$^6$ are independently hydrogen, halogen or C$_1$-C$_4$ alkyl
or in which R$^1$ and R$^2$, or R$^3$ and R$^4$, taken together are C$_2$-C$_5$ alkylene;
R$_7$ is halogen; C$_1$-C$_4$ alkyl; or nitro;
R$^8$, R$^9$, and R$^{10}$ independently are hydrogen or substituants including halogen; C$_1$-C$_4$ alkyl; C$_1$-C$_4$ alkoxy; trifluoromethoxy; C$_1$-C$_4$ haloalkyl
R$_b$S(O)$_n$ in which n is 0, 1 or 2; and R$_b$ is C$_1$-C$_4$ alkyl, C$_1$-C$_4$ haloalkyl, phenyl or benzyl;
and as an antidote compound therefor, a nonphytotoxic antidotally effective amount of a compound selected from amides of haloalkanoic acids; and 1,8 naphthalic anhydride, wherein said compound is antidotally active with said herbicide and wherein the weight ratio of herbicide to antidote is from about 0.0:1 to about 30:1.

2. A herbicide composition as defined in claim 1 wherein said antidote is an amide of haloalkanoic acid.

3. A herbicide composition as defined in claim 2 wherein said haloalkanoic acid is dichloroacetic acid.

4. A herbicide composition as defined in claim 2 wherein said antidote is an amide wherein the nitrogen atom thereof is in an oxazolidine.

5. A herbicide composition as defined in claim 1 wherein said antidote is 1,8-naphthalic anhydride.

6. A herbicide composition as defined in claim 1 wherein said antidote compounds correspond to the formula

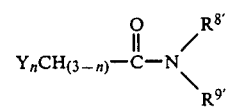

in which n is 1 or 2, Y is chlorine or bromine and R$^{8'}$ and R$^{9'}$ are independently C$_1$-C$_{12}$ alkyl, C$_2$-C$_{12}$ alkenyl, dialkoxyalkyl wherein the alkoxy and alkyl groups each have 1-4 carbon atoms and R$^{8'}$ and R$^{9'}$ taken together are C$_1$-C$_4$ alkyleneoxy alkylene.

7. A herbicide composition as defined in claim 1 wherein said antidote compounds correspond to the formula

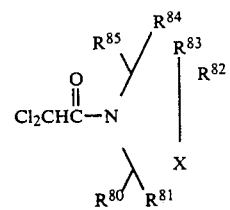

wherein formula, R$^{80}$, R$^{81}$, R$^{82}$, R$^{83}$, R$^{84}$ and R$^{85}$ are independently hydrogen, lower alkyl, or R$^{80}$ and R$^{81}$ taken together form a alkylene group; and X is oxygen or sulfur optionally substituted by one or two methyl groups and X is oxygen or sulfur.

8. A herbicide composition as defined in claim 1 wherein said herbicidal active ingredient is a compound of the formula

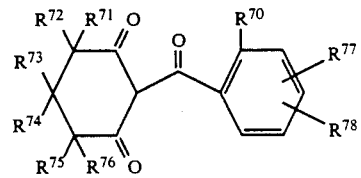

wherein
R$^{70}$ is halogen; C$_1$-C$_2$ alkyl; nitro
R$^{71}$ is hydrogen or C$_1$-C$_4$ alkyl; or halogen
R$^{72}$ is hydrogen or C$_1$-C$_4$ alkyl;
R$^{71}$ and R$^{72}$ together are C$_2$-C$_5$ alkylene;
R$^{73}$ is hydrogen; C$_1$-C$_4$ alkyl
R$^{74}$ is hydrogen; C$_1$-C$_4$ alkyl;
R$^{75}$ is hydrogen; halogen or C$_1$-C$_4$ alkyl;
R$^{76}$ is halogen, nitro, cyano, trifluoromethyl, and
R$^{77}$ and R$^{78}$ independently are (1) hydrogen; (2) halogen; (3) C$_1$-C$_4$ alkyl; (4) C$_1$-C$_4$ alkoxy; (5) trifluoromethoxy; (6) cyano; (7) nitro; (8) C$_1$-C$_4$ haloalkyl.

9. A method of reducing injury to crops by a herbicide of the formula

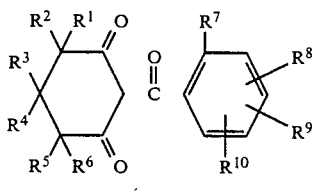

in which
R$^1$, R$^2$, R$^3$, R$^4$, R$^5$ and R$^6$ are independently hydrogen or C$_1$–C$_4$ alkyl or
in which R$^1$ and R$^2$, or R$^3$ and R$^4$, taken together are C$_2$–C$_5$ alkylene;
R$^7$ is nitro;
R$^8$, R$^9$ and R$^{10}$ independently are hydrogen or substituants including halogen; C$_1$–C$_4$ alkyl; C$_1$–C$_4$ alkoxy; trifluoromethoxy; C$_1$–C$_4$ haloalkyl;
which comprises applying to the soil, crop or seed crop a non-phytotoxic antidotally effective amount of a compound selected from the group consisting of amides of haloalkanoic acids, wherein said compound is antidotally active with said herbicide and wherein the weight ratio of herbicide to antidote compound is from about 0.1:1 to about 30:1.

10. The method of claim 8 wherein said method is a seal treatment.

11. The method of claim 8 wherein said method is a soil incorporation treatment.

12. The method of claim 9 wherein said antidote is an amide of haloalkanoic acid.

13. The method of claim 12 wherein said haloalkanoic acid is dichloroacetic acid.

14. The method of claim 9 wherein said antidote is an amide of haloalkanoic acid wherein the nitrogen atom is in an oxazolidine.

15. The method of reducing injury to crops as defined in claim 9 wherein said herbicide is of the formula

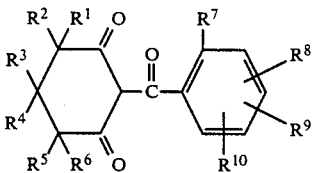

in which
R$^1$, R$^2$, R$^3$, R$^4$, R$^5$ and R$^6$ are independently hydrogen or C$_1$–C$_4$ alkyl;
or in which R$^1$ and R$^2$, or R$^3$ and R$^4$, taken together are C$_2$–C$_5$ alkylene;
R$_7$ is nitro;
R$^8$, R$^9$ and R$^{10}$ independently are hydrogen or substituents including halogen; C$_1$–C$_4$ alkyl; C$_1$–C$_4$ alkoxy; trifluoromethoxy; C$_1$–C$_4$ haloalkyl;
and said antidote compound corresponds to the formula

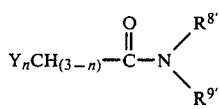

in which n is 1 or 2, Y is chlorine or bromine and R$^{8'}$ and R$^{9'}$ are independently C$_1$–C$_{12}$ alkyl, C$_2$–C$_{12}$ alkylene, dialkoxyalkyl wherein the alkoxy and alkyl groups each have 1–4 carbon atoms and R$^{8'}$ and R$^{9'}$ taken together are C$_1$–C$_4$ alkyleneoxy alkylene.

16. The method of reducing injury to crops as defined in claim 9 wherein said herbicide is of the formula

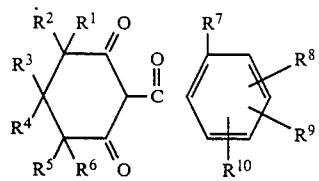

in which
R$^1$, R$^2$, R$^3$, R$^4$, R$^5$ and R$^6$ are independently hydrogen or C$_1$–C$_4$ alkyl;
or in which R$^1$ and R$^2$, or R$^3$ and R$^4$, taken together are C$_1$–C$_4$ alkylene;
R$_7$ is nitro;
R$^8$, R$^9$ and R$^{10}$ independently are hydrogen or substituents including halogen; C$_1$–C$_4$ alkyl; C$_1$–C$_4$ alkoxy; trifluoromethoxy; C$_1$–C$_4$-haloalkyl
and said antidote compound corresponds to the formula

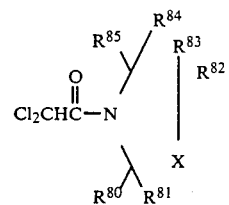

wherein R$^{80}$, R$^{81}$, R$^{82}$, R$^{83}$, R$^{84}$ and R$^{85}$ are independently hydrogen, lower alkyl or R$^{80}$ and R$^{81}$ taken together form a alkylene group; and X is oxygen optionally substituted by one or two methyl groups.

17. The method of reducing injury to crops as defined in claim 9 wherein said herbicide is of the formula

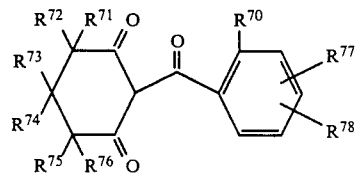

wherein
R$^{70}$ is nitro;
R$^{71}$ is hydrogen, C$_1$–C$_4$ alkyl or halogen;
R$^{72}$ is hydrogen or C$_1$–C$_4$ alkyl; or
R$^{71}$ and R$^{72}$ taken together are C$_2$–C$_5$ alkylene;
R$^{73}$ is hydrogen or C$_1$–C$_4$ alkyl;
R$^{74}$ is hydrogen or C$_1$–C$_4$ alkyl;
R$^{75}$ is hydrogen, halogen or C$_1$–C$_4$ alkyl;
R$^{76}$ is halogen, nitro, cyano, trifluoromethyl;
R$^{77}$ and R$^{78}$ independently are (1) hydrogen; (2) halogen; (3) C$_1$–C$_4$ alkyl; (4) C$_1$–C$_4$ alkoxy; (5) trifluoromethoxy; (6) cyano; (7) nitro; (8) C$_1$–C$_4$ haloalkyl.

18. The composition of claim 1 wherein said acylated 1,3-dicarbonyl compound contains from about 11 carbon atoms to about 42 carbon atoms, inclusive.

19. The method of claim 9 wherein said acylated 1,3-dicarbonyl compound contains from about 11 carbon atoms to about 42 carbon atoms, inclusive.

20. The method of claim 9 wherein said method is a preemergence treatment.

21. The method of claim 9 wherein said method is a surface treatment.

* * * * *

UNITED STATES PATENT AND TRADEMARK OFFICE
CERTIFICATE OF CORRECTION

PATENT NO. : 4,938,796                    Page 1 of 6
DATED     : July 3, 1990
INVENTOR(S) : Lawrence L. Buren, Joanna K. Hsu, Michael P. Ensminger,
Charles J. Duerksen, Nicholas N. Poletika and Benjamin P. Rodriquez It is certified that error appears in the above-indentified patent and that said Letters Patent is hereby corrected as shown below:

In Column 55, line 50, the formula

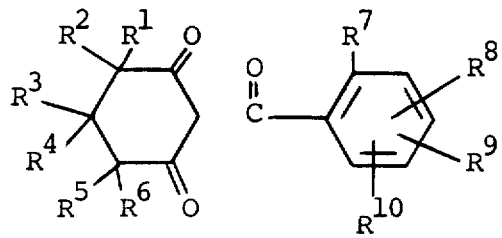

should read

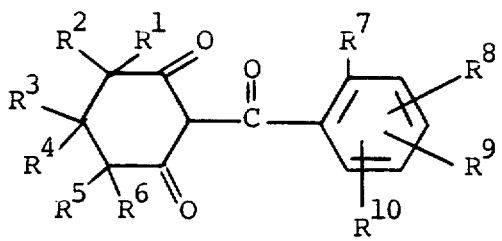

UNITED STATES PATENT AND TRADEMARK OFFICE
CERTIFICATE OF CORRECTION

PATENT NO. : 4,938,796  
DATED : July 3, 1990  
INVENTOR(S) : Lawrence L. Buren, Joanna K. Hsu, Michael P. Ensminger, Charles J. Duerksen, Nicholas N. Poletika and Benjamin P. Rodriquez It is certified that error appears in the above-indentified patent and that said Letters Patent is hereby corrected as shown below:

In Column 56, line 28-37, the formula

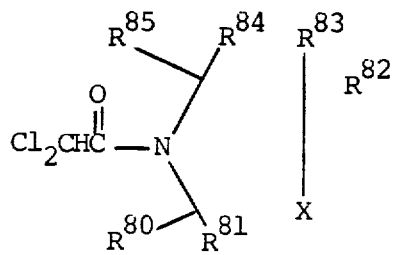

should read

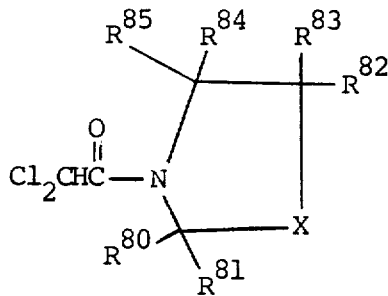

UNITED STATES PATENT AND TRADEMARK OFFICE
CERTIFICATE OF CORRECTION

PATENT NO. : 4,938,796                              Page 3 of 6

DATED       : July 3, 1990

INVENTOR(S) : Lawrence L. Buren, Joanna K. Hsu, Michael P. Ensminger,
Charles J. Duerksen, Nicholas N. Poletika and Benjamin P. Rodriquez It is certified that error appears in the above-indentified patent and that said Letters Patent is hereby corrected as shown below:

In Column 57, line 5-10, the formula

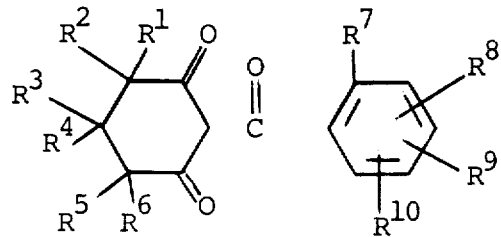

should read

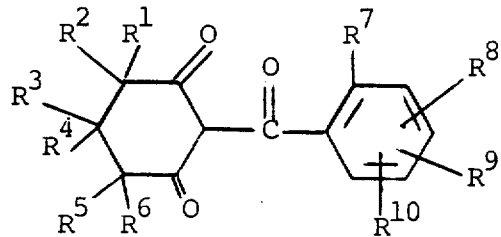

UNITED STATES PATENT AND TRADEMARK OFFICE
CERTIFICATE OF CORRECTION

PATENT NO. : 4,938,796            Page 4 of 6

DATED : July 3, 1990

INVENTOR(S) : Lawrence L. Buren, Joanna K. Hsu, Michael P. Ensminger, Charles J. Duerksen, Nicholas N. Poletika and Benjamin P. Rodriquez It is certified that error appears in the above-indentified patent and that said Letters Patent is hereby corrected as shown below:

In Column 57, line 29, the word "seal" should read --seed--.

UNITED STATES PATENT AND TRADEMARK OFFICE
CERTIFICATE OF CORRECTION

PATENT NO. : 4,938,796

DATED : July 3, 1990

INVENTOR(S) : Lawrence L. Buren, Joanna K. Hsu, Michael P. Ensminger, Charles J. Duerksen, Nicholas N. Poletika and Benjamin P. Rodriquez It is certified that error appears in the above-indentified patent and that said Letters Patent is hereby corrected as shown below:

In Column 58, lines 8-15, the formula

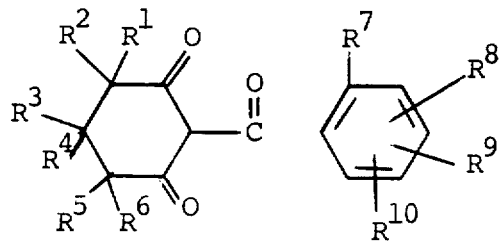

should read

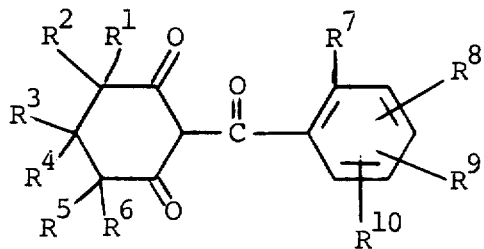

UNITED STATES PATENT AND TRADEMARK OFFICE
CERTIFICATE OF CORRECTION

PATENT NO. : 4,938,796
DATED : July 3, 1990
INVENTOR(S) : Lawrence L. Buren, et al.

It is certified that error appears in the above-identified patent and that said Letters Patent is hereby corrected as shown below:

In Column 58, lines 28-39, the formula

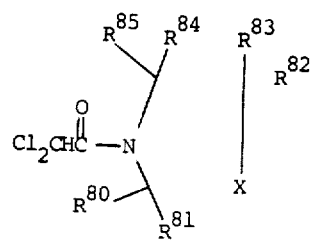

should read

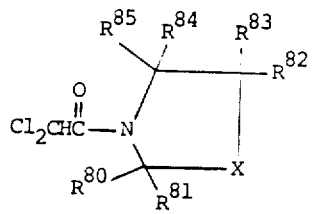

Signed and Sealed this

Seventh Day of June, 1994

Attest:

BRUCE LEHMAN

Attesting Officer        Commissioner of Patents and Trademarks